United States Patent [19]

Ayer et al.

[11] 4,427,591

[45] Jan. 24, 1984

[54] REDUCED A RING-$\Delta^{9(11)}$-CORTICOIDS

[75] Inventors: Donald E. Ayer; Carl A. Schlagel, both of Kalamazoo, Mich.

[73] Assignee: The Upjohn Company, Kalamazoo, Mich.

[21] Appl. No.: 298,985

[22] Filed: Sep. 3, 1981

Related U.S. Application Data

[62] Division of Ser. No. 117,401, Mar. 31, 1980, Pat. No. 4,318,853.

[51] Int. Cl.$^3$ ................................................ C07J 7/00
[52] U.S. Cl. ...................... 260/397.45; 260/239.55 R; 260/239.55 D; 424/243
[58] Field of Search .................................... 260/397.45

[56] References Cited

U.S. PATENT DOCUMENTS 3,055,922  3/1970  Krakower et al. ............. 260/397.45
3,992,422  11/1976  Green et al. ................... 260/397.45
4,336,200  6/1982  Ayer et al. ..................... 260/397.45

Primary Examiner—Elbert L. Roberts
Attorney, Agent, or Firm—Bruce Stein

[57] ABSTRACT

17α-Acyloxy-5β-pregnanes (I) and 17α-acyloxy-5α-pregnanes (IV) have an excellent activity split providing high topical anti-inflammatory activity with very low systemic side effects.

60 Claims, No Drawings

REDUCED A RING-Δ⁹⁽¹¹⁾-CORTICOIDS

This is a division of application Ser. No. 117,401, filed Jan. 31, 1980 now U.S. Pat. No. 4,318,853.

BACKGROUND OF THE INVENTION

Numerous patents disclose various 17α-hydroxy corticoids which are useful as topical anti-inflammatory agents. Various substituents and/or derivatives such as 2α-methyl, 9α-fluoro, 6α-methyl, $\Delta^{1,4}$, 16-alkyl and 6α-fluoro have been reported to enhance pharmacological activity.

In general, those substituents which enhance corticoid activity such as 6α-methyl, $\Delta^{1,4}$ or 9α-fluoro were also found to enhance resistance of the 17α-hydroxy corticoid to metabolic transformation by the liver; that is the more potent substituted steroids were more slowly metabolized.

In general, 21-halo steroids have been reported as providing enhanced activity and/or favorable ratio of topical anti-inflammatory activity to systemic side effects, see U.S. Pat. Nos. 3,721,687 and 3,992,422. U.S. Pat. No. 4,051,055 discloses 21-halo steroids but not as topical anti-inflammatory agents but as intermediates in the synthesis of corticoids. U.S. Pat. No. 3,502,700 discloses various 21-halo steroids as useful for their progestational activity and does not mention topical anti-inflammatory activity. All of the above 21-halo steroids were $\Delta^4$- and $\Delta^{1,4}$-9,21-dihalo-11β-hydroxy-16-alkyl steroids. A number of these are mentioned as having an "... especially favourable topical anti-inflammatory activity and/or ratio of topical anti-inflammatory activity is glucocorticoid activity ...". In the specification of U.S. Pat. No. 3,721,687 a number of substituents are identified as being preferred or especially preferred. These include $\Delta^{1,4}$; 9α-chloro-11β-hydroxy-16-methyl-17-propionate; 9α-fluoro-11-hydroxy-16α-methyl-17-esters with at least 3 carbon atoms and 9α-fluoro-11-keto-16-methyl or -16-methylene steroids. A particularly preferred compound appears to be "9α,21-difluoro-16-methylene-17-propionyloxy-1,4-diene-3,11,20-trione."

Virtually all the cortical steroids disclosed for topical anti-inflammatory activity are $\Delta^4$ or $\Delta^{1,4}$ steroids. U.S. Pat. No. 3,055,922 discloses a series of 5α-steroids which were alleged to retain the topical anti-inflammatory activity of the corresponding $\Delta^4$- or $\Delta^{1,4}$-steroids while the systemic activity was for all practical purposes eliminated. The applicants have now established that the "5α" steroids of U.S. Pat. No. 3,055,922 were actually "5β." This matter will be discussed fully in the Detailed Description of the invention.

Therefore, both U.S. Pat. Nos. 3,721,687 and 3,055,922 disclose a split between the topical anti-inflammatory activity and the systemic activity. However, U.S. Pat. No. 3,721,687 discloses that 17α-acyloxy-$\Delta^{1,4}$-steroids have a good activity split while U.S. Pat. No. 3,055,922 discloses that 17α-hydroxy-5α-steroids have a good activity split. The present invention discloses that 17α-acyloxy-5α-steroids and 17α-acyloxy-5β-steroids surprisingly and unexpectedly have an excellent activity split, and high topical anti-inflammatory topical/systemic ratio.

German Offen No. 2,905,674 discloses a process of transforming a 5α-pregnane to the corresponding $\Delta^{1,4}$-17α-acylate which is the opposite of the present invention. The steps in the procedure include (1) protection of the 11β-hydroxyl group as a trimethylsilyl (TMS) derivative (Example 1), (2) esterification of the 17α-hydroxyl group to give a 5α-17α-acyl-11β-TMS steroid (Example 2), (3) dehydrogenation (oxidation) of the 5α-A ring to a $\Delta^{1,4}$-A ring (Example 3) and (4) removal of the TMS protecting group (Example 4). In this process a 5α-17α-acyl steroid is disclosed but it does not have a free 11β-hydroxyl group. In addition, the compound is not disclosed as having any useful pharmacological activity but only as an intermediate.

BRIEF DESCRIPTION OF THE INVENTION

Disclosed are 17α-acyloxy-5β-steroids (I) and 17α-acyloxy-5α-steroids (IV) which have an excellent split between topical anti-inflammatory activity and systemic activity.

Also disclosed are 17α-acyloxy-5β-9,11-epoxy steroids (II) and 17α-acyloxy-5β-$\Delta^{9(11)}$-steroids (III) which are useful intermediates in the preparation of the 17α-acyloxy-5β-steroids (I) of the present invention.

Further disclosed are 17α-acyloxy-5α-21-hydroxy steroids (IVE) which are useful intermediates in the preparation of the 17α-acyloxy-5α-steroids (IV) of the present invention.

Disclosed is a process for preparing 17α-acyloxy-5β-steroids (I) which comprises (1) hydrogenating the corresponding $\Delta^4$- or $\Delta^{1,4}$-steroid (IA) in the presence of a hydrogenating catalyst and (2) separating the 5β-isomer from the 5α-isomer.

Also disclosed are processes for preparing the 17α-acyloxy-5β-9,11-epoxy-steroid (II) and the 17α-acyloxy-5β-$\Delta^{9(11)}$-steroid (III) which comprises (1) hydrogenating the corresponding $\Delta^4$- or $\Delta^{1,4}$-steroids (IIA and IIIA) respectively, in the presence of a hydrogenating catalyst and (2) separating the 5β-isomer from the 5α-isomer.

Further disclosed is a process for the preparation of a 17α,21-dihydroxy-5α-steroid (IVD) which comprises (1) blocking the side chain of a $\Delta^4$-17α,21-dihydroxy steroid (IVA) by reaction with an aldehyde of the formula R—CHO to give a $\Delta$-17,21-blocked steroid (IVB), (2) reducing the $\Delta^4$-double bond by reaction with a metal-amine to give the 17,21-blocked-5α-steroid (IVC) and (3) removing the side chain blocking group.

DETAILED DESCRIPTION OF THE INVENTION

The 17α-acyloxy-5β-corticoids (I) of the present invention are generally most readily by hydrogenating the corresponding $\Delta^4$- or $\Delta^{1,4}$-steroids of formula (IA) which are either well-known to those skilled in the art or can be readily prepared by well-known procedures from known compounds.

The $\Delta^4$- or $\Delta^{1,4}$-steroid (IA) starting material is subjected to hydrogenation as is well-known to those skilled in the art. The $\Delta^4$ or $\Delta^{1,4}$-steroid (IA) is dissolved in a suitable organic solvent such as ethyl acetate, acetone, THF, toluene and alcohols such as methanol or ethanol. Preferred solvents are ethyl acetate, THF and acetone. The reaction is performed in the presence of a hydrogenation catalyst. These catalysts are well known to those skilled in the art and include, for example, heterogenous catalysts such as palladium on carbon, platinum on carbon, platinum dioxide, palladium on barium carbonate or palladium on calcium carbonate, rhodium on alumina, rhodium on carbon, palladium on barium sulfate or palladium on zinc oxide and the like. Soluble catalysts such as tris(triphenylphosphine) rhodium (I) chloride may also be employed. In addition strong acid or strong base catalysts may optionally be used. Suitable strong acids include mineral acids such as hydrogen chloride or perchloric acid and organic acids such as p-toluene sulfonic acid or 2,4-dinitrobenzene sulfonic acid. Suitable strong bases include inorganic bases such as sodium hydroxide or potassium hydroxide and organic bases such as triethylamine or 1,4-diazabicyclo[2.2.2]octane (Dabco). The reaction is performed under hydrogen using a pressure of 1–10 atmospheres. One to two atmospheres is convenient. Higher pressure can be utilized if desired.

The reaction is performed at 20°–25° until the desired uptake of hydrogen is complete. Lower or higher temperatures are suitable but room temperature is most convenient.

When the uptake of hydrogen is complete, the mixture is filtered and the filtrate is concentrated under reduced pressure. The concentrate contains a mixture of the $5\alpha$ and $5\beta$ isomers. The $5\beta$ isomer is formed stereospecifically when $R_9$ is fluorine. The $5\beta$ isomer predominates when the C ring functionality is 9,11-epoxy (IIA) or $\Delta^{9(11)}$ (IIIA). A roughly equal mixture of $5\beta$ and $5\alpha$ isomers is formed when $R_9$ is hydrogen and $R_{11}$ is hydroxyl. This ratio is dependent on the experimental conditions and the specific structure of the hydrogenation substrate.

The mixture of $5\beta$ and $5\alpha$ isomers is separated by chromatography as is well-known to those skilled in the art. Adsorbents such as silica gel, Florisil and alumina may be employed. Various organic solvents such as methanol, acetone, ethyl acetate, ether, methylene chloride, hexane, Skellysolve B and chloroform are used for elution either alone or in combination. Those fractions containing the steroid product with the $5\beta$ configuration as determined by CMR are combined and concentrated to give the desired 17$\alpha$-acyloxy-5$\beta$-product (I). If desired further purification is achieved by crystallization from a suitable solvent.

When a $\Delta^4$- or a $\Delta^{1,4}$-steroid (IA–IIIA) is hydrogenated, two isomeric products, $5\alpha$ and $5\beta$ (I–III), can be and are formed. U.S. Pat. No. 3,055,922 reported obtaining only the $5\alpha$-isomer analytically pure and in almost quantitative yield upon hydrogenation of $\Delta^4$- and $\Delta^{1,4}$-steroids with the appropriate noble metal catalyst. U.S. Pat. No. 3,055,922 was filed in 1961. In 1972 J. L. Gough, J. P. Guthrie and J. P. Stothers [J.C.S. Chem. Comm. 979 (1972)] reported a method of determining the stereochemistry of the A/B ring junction by CMR. These authors reported that when the A/B ring junction is cis (5$\beta$), the $C_{19}$ carbon atom is less shielded by about 11–12 ppm. Based on this evidence and their own experimentation the applicants have determined that the predominate isomer produced when a $\Delta^4$- or $\Delta^{1,4}$-steroid is hydrogenated under the conditions set forth in this invention is $5\beta$ and not $5\alpha$ as reported in U.S. Pat. No. 3,055,922. It is realized that at the time of filing of the patent application for U.S. Pat. No. 3,055,922, CMR spectroscopy was not available.

Further, E. L. Shapiro et al. (J. Chem. Soc., Chem. Comm. 1976, 961) in 1976 reported that hydrogenation of $\Delta^4$- and $\Delta^{1,4}$-3-keto-9$\alpha$-fluoro gave exclusively the 5$\beta$-isomer.

A preferred way to produce the 5$\beta$-steroid (I) is by hydrogenation of the corresponding $\Delta^4$- or $\Delta^{1,4}$-steroid (IA, where $R_9$ is fluorine or chlorine) as disclosed in Chart A. An alternative process is to hydrogenate either the 9,11-epoxy-steroid (IIA) or the $\Delta^{9(11)}$-steroid (IIIA) to the corresponding 9,11-epoxy-5$\beta$-steroid (II) or the $\Delta^{9(11)}$-5$\beta$-steroid (III). The 17$\alpha$-acyloxy-5$\beta$-9,11-epoxy steroid (II) may be converted to the desired 17$\alpha$-acyloxy-5$\beta$-steroid (I, $R_9$ is chlorine and $R_{11}$ is hydroxyl) under carefully controlled reaction conditions (see Example 129). The 17$\alpha$-acyloxy-5$\beta$-$\Delta^{9(11)}$steroid (III) may be readily converted to the desired 17$\alpha$-acyloxy-5$\beta$-steroid (I, $R_9$ is chlorine and $R_{11}$ is chlorine) by means well known to those skilled in the art.

It is possible to prepare 5$\beta$-starting materials from bile acid intermediates. For example, 11$\alpha$,17$\alpha$,21-trihydroxy-16$\beta$-methyl-5$\beta$-pregnane-3,20-dione 21-acetate [E. P. Oliveto et al., J. Amer. Chem. Soc. 80, 6687 (1958)] may readily be converted to 17$\alpha$,21-dihydroxy-16$\beta$-methyl-5$\beta$-pregn-9(11)-ene-3,20-dione 21-acetate, an intermediate for preparation of 17$\alpha$-acyloxy-5$\beta$-$\Delta^{9(11)}$-steroids (III).

Alternatively one skilled in the art can start with a variety of $\Delta^4$- or $\Delta^{1,4}$-steroids (IA) and hydrogenate to produce the corresponding 5$\beta$- and 5$\alpha$-steroids and then modify the B, C, or D ring of the steroid to obtain the desired pharmacologically active 17$\alpha$-acyloxy-5$\beta$-steroid (I) or 17$\alpha$-acyloxy-5$\alpha$-steroid (IV).

The process of hydrogenation of the $\Delta^4$ or $\Delta^{1,4}$-steroids (IA) has been performed with a large variety of substituents, attached to the B, C and D rings of the steroid. Both $\Delta^4$- (Example 74) and $\Delta^{1,4}$-steroids (Examples 53, 73 and 80) are suitable starting materials for hydrogenation. For example, 9$\alpha$-fluoro-11$\beta$,17$\alpha$,21-trihydroxy-16$\beta$-methyl-5$\beta$-pregnane-3,20-dione 17,21-propionate was prepared from both the corresponding $\Delta^4$-steroid (Example 74) and the corresponding $\Delta^{1,4}$-steroid (Example 75). Both 11$\beta$-hydroxyl (Examples 53, 73, 74, 76 and 78) and 11-keto (Example 80) steroids have been hydrogenated to give the corresponding 5$\beta$-steroid. At C-16, 16$\beta$-methyl (Examples 53, 73, 74 and 176), 16$\alpha$-methyl (Examples 104, 107, 113 and 120) and 16-hydrogen (Examples 78, 80 and 114) steroids all have been used. At C-9, 9$\alpha$-chloro (Examples 115–117), 9,11-epoxy (Example 125) and $\Delta^{9(11)}$ (Examples 38 and 44) all can be used. At C-6 both 6$\alpha$-methyl (Example 80) and 6$\alpha$-fluoro (Example 81) have been used. At C-21 various functionalities such as hydroxyl (Example 89), ester (Examples 74, 81, 113), chlorine (Examples 53, 73 and 80), mesylate (Examples 76 and 104) and fluorine (Example 117) all can be used.

A given 5$\beta$,17$\alpha$-acylate (I) can be prepared by processes other than hydrogenation of the corresponding $\Delta^4$- or $\Delta^{1,4}$-precursor. For example, 21-chloro-9$\alpha$-fluoro-16$\beta$-methyl-11$\beta$,17$\alpha$-dihydroxy-5$\beta$-pregnane-3,20-dione 17-propionate (I) was prepared from the corresponding $\Delta^{1,4}$-steroid (IA) by hydrogenation, see Example 53. The same compound was also prepared by starting with the corresponding $\Delta^{1,4}$-17$\alpha$-hydroxy-21-benzoate, 9$\alpha$-fluoro-11$\beta$,17$\alpha$,21-trihydroxy-16$\beta$-methylpregna-1,4-diene-3,20-dione 21-benzoate and subjecting it to the following reactions: hydrogenation (Preparation 2), hydrolysis of the 21-benzoate (Example 22), formation of the 17-propionate (Example 24), formation of the 21-mesylate (Example 29) and displacement of the 21-mesylate (Example 34) by chloride.

Therefore, hydrogenation of the $\Delta^4$- or $\Delta^{1,4}$-steroid may take place early in the synthesis with other substitution and/or modification to be performed after hydrogenation or the steroid molecule can be substituted and/or modified so that the last step in the synthesis is the reduction of the unsaturation in the steroid A ring.

Generally, the $\Delta^4$ or $\Delta^{1,4}$-steroids (IA) to be hydrogenated have at the 9α-position a fluorine atom and at the 11β-position a hydroxyl group. However, $\Delta^4$ and $\Delta^{1,4}$-steroids having at the 9 and 11 positions a double bond, $\Delta^{9(11)}$, can also be hydrogenated to produce the corresponding 5β-pregnane. The $\Delta^{9(11)}$-5β-steroids are useful to prepare 9α,11β-dichloro-5β-steroids (I), see Examples 38–43 and 44–52 (9α,11β,21-trichloro-5β-steroids). Likewise, $\Delta^4$- and $\Delta^{1,4}$-steroids having at the 9 and 11 positions an epoxy group (9,11-epoxy) are useful to prepare 9α-chloro-11β-hydroxy-5β-steroids. The 9,11-epoxy-5β-steroids are not useful to prepare 9α-fluoro-11β-hydroxy-5β-steroids because when the epoxide is reacted with hydrogen fluoride only a few percent of the desired 9α-fluoro-11β-hydroxy-5β-steroid are produced.

The 9α-chloro-11β-hydroxy-5β-steroids (I) are obtained from the corresponding 9,11-epoxy-5β-steroids by reaction with hydrogen chloride, hydrogen chloride in the presence of a quaternary amine chloride (such as tetrabutylammonium chloride) or dichlorobis (benzonitrile) palladium (II) under carefully controlled conditions.

The 5α-steroids (IV) are produced in small amounts during hydrogenation of the corresponding $\Delta^4$- or $\Delta^{1,4}$-steroid (IA). However, a preferred route to prepare the 5α-steroids (IV) is not by hydrogenation of the corresponding $\Delta^4$- or $\Delta^{1,4}$-steroid (IA) but rather by a stereoselective metal-amine reduction of a $\Delta^4$- or $\Delta^{1,4}$-steroid. The steroid is reduced with sodium in ammonia or lithium in ammonia or alkyl amines such as methylamine, ethylamine or ethylenediamine, preferably with lithium in liquid ammonia. Before performing the lithium-ammonia reduction the pregnane side chain of the $\Delta^4$- or $\Delta^{1,4}$-steroid must be protected. The side chain is conveniently protected as a 17,20;20,21-bisdioxy (preferably bismethylenedioxy) derivative as is well-known to those skilled in the art (U.S. Pat. Nos. 2,888,456 and 2,888,457).

The $\Delta^4$- or $\Delta^{1,4}$-steroid in an inert organic diluent such as THF, diethyl ether or dioxane is added to a solution of lithium in liquid ammonia at $-60°$ to $-80°$. The reaction is monitored by TLC and when complete (about 1 hour), the reaction is worked up as is well-known to those skilled in the art. Following the stereospecific reduction, the hydroxy protecting groups are removed, as is well-known to those skilled in the art, by acid hydrolysis. Acetic acid is a suitable acid. Alternatively, the 5α-starting materials may be obtained from a sapogenin which possesses the desired 5α-configuration. For example, 3β-hydroxy-5α-pregna-9(11),16-dien-20-one 3-acetate derived from hecogenin is a versatile starting material for preparation of 5α-steroids (IV) of this invention as will be apparent to one skilled in the art. This intermediate has been converted to 17α,21-dihydroxy-16β-methyl-5α-pregn-9(11)-ene-3,20-dione 21-acetate by J. Attenburrow et al (J. Chem. Soc. 1961, 4547).

Following reduction of the $\Delta^4$ or $\Delta^{-1,4}$ double bond to produce the 5α-steroid and the hydrolysis of the blocking groups to produce the 17α,21-dihydroxy-$\Delta^{9(11)}$-5α-steroid (Preparation 18) the steroid is acylated at C-17. From this point, a large number of modifications at C-9, 11, and 21 can be made to produce the desired 5α-steroid (IV). For example, if a 21-chloro-5α-steroid (IV) is desired, the 21-hydroxyl group is transformed to the mesylate (see Example 205) and subsequently to the 21-chloro substituent (see Example 206, Step 3, and Example 251, Step 1). If a 5α-steroid (IV) unsubstituted at C-21 is desired, it is produced from a 21-chloro steroid (see Example 221). If 9α,11β-dichloro-5α-steroids (IV) are desired, they are produced from the corresponding $\Delta^{9(11)}$-5α-steroids as is well known to those skilled in the art (see Examples 251, Step 2 and 374). Many topically active anti-inflammatory steroids have a fluorine atom at C-9. If a 5α-steroid with a hydrogen atom at C-9 is desired, it can be readily prepared from the corresponding 9α-bromo-5α-steroid (see Examples 266 and 383). The 21-phosphates (Examples 314–328), 21-disodium phosphate (Examples 329–343), 21-hemisuccinates (Examples 344–358) and 21-sodium hemisuccinates (Examples 359–373) are produced by means well known to those skilled in the art.

The 17α-acyloxy-5β-corticosteroids (I) and 17α-acyloxy-5α-corticosteroids (IV) of the present invention are therapeutically useful anti-inflammatory agents when applied topically or administered locally to warm-blooded animals responsive to treatment with anti-inflammatory corticosteroids. The 17α-acyloxy-5β-corticosteroids (I) and 17α-acyloxy-5α-corticosteroids (IV) are especially useful for topical and local administration because they possess the unique combination when applied locally of high potency, low systemic activity, thus producing less unwanted systemic corticoid action for a given amount of topical-local anti-inflammatory activity relative to corticoids now employed therapeutically.

The 17α-acyloxy-5β-corticosteroids (I) and 17α-acyloxy-5α-corticosteroids (IV) are administered topically to the inflamed skin, eyes, external ears and mucous membranes of the mouth, nose, respiratory tract, vagina, rectum and colon. They are applied or instilled to these areas as drug suspensions or solutions in the usual dosage forms such as solutions, lotions, creams, ointments, gels, pastes, aerosols, bandages or tape, drops, enemas, suppositories, etc. For the therapy of asthma, allergic rhinitis and other inflammatory respiratory disorders, the usual dosage forms such as aerosols or powders, solutions and suspensions for inhalation are employed.

The 17α-acyloxy-5β-corticosteroids (I) and 17α-acyloxy-5α-corticosteroids (IV) are also useful for local intralesional therapy by intracavity (e.g., intra-articular) or soft tissue injection of solution, suspension or solution-suspension dosage forms. Also useful for the therapy of secondarily infected and inflamed conditions, particularly of the skin, eyes, external ear canals, rectum and vagina, are combination dosage forms of the 17α-acyloxy-5β-corticosteroids (I) or 17α-acyloxy-5α-corticosteroids (IV) and antifungal and/or antibacterial agents such as clotrimazole, dichloroxime, miconazole, neomycin, gentamycin, clindamycin, etc.

The water soluble esters (pharmaceutically acceptable salts) of 21-hemisuccinate or 21-phosphate are useful in eye and ear drops, rectal and vaginal formulations, for inhalation and for intracavity injection.

The concentration and dosage regimen of the dosage form used and the frequency of administration will depend upon the particular location and condition treated, the severity of the inflamed lesion, the potency of the particular 17α-acyloxy-5β-corticosteroids (I) and 17α-acyloxy-5α-corticosteroids (IV), the phase and natural course of the inflamation, the age and condition of the patient, and other factors known to practitioners skilled in the management of cutaneous and local inflammatory diseases.

The drug concentration ranges, and the dosage regimens of 17α-acyloxy-5β-corticosteroids (I) and 17α-acyloxy-5α-corticosteroids (IV) administered topically (locally) on inflammatory lesions of the skin, nostrils, vagina, rectum, colon and external ears are about 0.005% to about 2.5% with one to four daily applications. Generally preferred concentrations are from 0.01% to 0.2%. These same concentration ranges are used in the eyes, but with one to eight daily applications or instillations, according to phase and disease severity. For the therapy of asthma or other inflammations of the respiratory tract, two to three daily inhalations or sprays, each containing from 0.001 to 2.0 mg. of corticosteroid are used. From 1.0 to 100 mg. doses of the 17α-acyloxy-5β-corticosteroids (I) and 17α-acyloxy-5α-corticosteroids (IV) are administered for intralesional inflammation of joints, tissue cavities and soft tissues. The volume and frequency of the injections are dependent primarily on lesion size, severity and response to treatment.

Some examples of inflammatory diseases wherein the 17α-acyloxy-5β-corticosteroids (I) and 17α-acyloxy-5α-corticosteroids (IV) are useful topically and locally are (1) dermatoses such as psoriasis, atopic, neuro, contact and allergic dermatitis, lichen planus, alopecia areata and immune diseases (2) pruritus ani, vulva and rectal or colonic inflammation (3) conjunctivitis, superficial punctate keratitis and herpes zoster keratitis of the eyes (4) contact, allergic and selected infective otitis of the external ear canal and (5) allergic-inflammatory nasal and respiratory conditions such as rhinitis and asthma.

Some examples of conditions treated with the 17α-acyloxy-5β-corticosteroids (I) and 17α-acyloxy-5α-corticosteroids (IV) by injection into local lesions are (1) rheumatoid arthritis, bursitis and peritendenitis and (2) alopecia areata, cystic acne, keloids, hypertrophic scarring conditions and localized, treatment-resistant type dermatitic lesions.

DEFINITIONS

The definitions and explanations below are for the terms as used throughout the entire patent application including both the specification and claims.

All temperatures are in degrees Centigrade.
TLC refers to thin-layer chromatography.
THF refers to tetrahydrofuran.
DMF refers to dimethylformamide.
SSB refers to a mixture of isomeric hexanes.
p-TSA refers to p-toluenesulfonic acid.
Saline refers to an aqueous saturated sodium chloride solution.
IR refers to infrared spectroscopy determined on a mineral oil mull of the sample.
CMR refers to 13C magnetic resonance spectroscopy, in deuterochloroform, chemical shifts of C-19 are reported in ppm (δ) downfield from TMS.
NMR refers to nuclear (Proton) magnetic resonance spectroscopy chemical shifts are reported in ppm (δ) downfield from TMS.
$[\alpha]_D^{25}$ refers to the angle of rotation of plane polarized light (specific optical rotation) of a 1% solution in dioxane at 25°.
When solvent pairs are used, the ratio of solvents used are volume/volume (v/v).
Pharmaceutically acceptable refers to those properties and/or substances which are acceptable to the patient from a pharmacological-toxicological point of view and to the manufacturing pharmaceutical chemist from a physical-chemical point of view regarding composition, formulation, stability, patient acceptance and bio-availability.

$R_2$ is a hydrogen, fluorine or chlorine atom or methyl group.
$R_6$ is a hydrogen, fluorine or chlorine atom or methyl group.
$R_7$ is a hydrogen, fluorine or chlorine atom.
$R_9$ is a hydrogen, fluorine or chlorine atom.
R is a hydrogen atom or alkyl group of 1 thru 4 carbon atoms.
$R_{11}$ is a chlorine or oxygen atom or hydroxyl group; when $R_{11}$ is a chlorine atom or hydroxyl group the $===$ between $R_{11}$ and $C_{11}$ is a single bond in the β-configuration and when $R_{11}$ is an oxygen atom the $===$ between $R_{11}$ and $C_{11}$ is a double bond.
$R_{16\alpha}$ is a hydrogen, fluorine or chlorine atom or methyl group.
$R_{16\beta}$ is a hydrogen atom or methyl group with the proviso that one of $R_{16\alpha}$ or $R_{16\beta}$ is a hydrogen atom.
$R_{17}$ is alkyl of 1 thru 6 carbon atoms, phenyl, p-methylphenyl, p-carboxyphenyl or p-carboalkoxyphenyl.
$R_{21}$ is a hydrogen, fluorine, chlorine or bromine atom or a $-OR_{21a}$ or $-OSO_2CH_3$ group.
$R_{21a}$ is a hydrogen atom, $-COR_{21b}$ or $-PO(OH)_2$ and pharmaceutically acceptable salts thereof.
$R_{21b}$ is alkyl of 1 thru 6 carbon atoms, phenyl, p-methylphenyl, or p-carboxyphenyl, p-carboalkoxyphenyl, $-CH_2CH_2COOH$ and pharmaceutically acceptable salts thereof.
~ indicates the attached group can be in either the α or β configuration.
$===$ is a single or double bond.

When the term "alkyl of 1 thru 6 carbon atoms" is used it includes the isomers thereof when they exist.

A hydrogenation catalyst is an additive which catalyzes the hydrogenation reaction to give the corresponding 5β-steroid (I–III).

Without further elaboration, it is believed that one skilled in the art can, using the preceding descriptions, practice the present invention to its fullest extent.

PREPARATIONS AND EXAMPLES

Preparation 1: 9α-Fluoro-11β,17α,21-trihydroxy-5β-pregnane-3,20-dione 21-acetate A mixture of 9α-fluoro-11β,17α,21-trihydroxypregna-1,4-diene-3,20-dione 21-acetate (20 g.) in acetone (200 ml.) is hydrogenated in the presence of palladium on carbon (5%, 1 g.) until the uptake of hydrogen is complete. The mixture is filtered and the filtrate is concentrated under reduced pressure. The concentrate is column chromatographed on silica gel (200 g.) packed in acetone-methylene chloride (10/90). Elution is performed with the same solvent system. The appropriate fractions are pooled and concentrated to give the product which upon crystallization from acetone-SSB gives 9α-fluoro-11β,17α,21-trihydroxy-5β-pregnane-3,20-dione 21-acetate, m.p. 215.5° (decomposition); $[\alpha]_D^{25}+72°$; CMR 26.66 δ; IR (mull) 3580, 3380, 1745, 1730, 1680, 1260, 1235, 1190, 1105, 1050, 990, and 905 cm$^{-1}$.

Preparation 2: 9α-Fluoro-11β,17α,21-trihydroxy-16β-methyl-5β-pregnane-3,20-dione 21-benzoate Following the general procedure of Preparation 1 and making noncritical variations but starting with 9α-fluoro-11β,17α,21-trihydroxy-16β-methylpregna-1,4- diene 3,20-dione 21-benzoate (betamethasone 21-benzoate) there is obtained 9α-fluoro-11β,17α,21-trihydroxy-16β-methyl-5β-pregnane-3,20-dione 21-benzoate, m.p. 205° (decomposition); CMR 26.66 δ; IR 3600, 3340, 1740, 1720, 1695, 1605, 1585, 1490, 1275, 1255, 1125, 1115, 1160, 1045 and 710 cm$^{-1}$ and [α]$_D$+109°.

Preparation 3: 17α,21-Dihydroxy-16β-methylpregna-1,4,9(11)-triene 3,20-dione

A mixture of 17α,21-dihydroxy-16β-methylpregna-1,4,9(11)-triene-3,20-dione 21-benzoate (U.S. Pat. No. 3,725,392, 20 g.) in methanol (600 ml.), methylene chloride (400 ml.) and methanolic sodium methoxide (25%, 13 ml.) is stirred at 20°–25° for one hour under an inert atmosphere. The reaction mixture is then acidified with acetic acid (4 ml.), concentrated under reduced pressure to about 320 ml. and diluted with water (320 ml.) in methanol (100 ml.). The mixture is extracted with SSB, and then the aqueous methanol phase is concentrated under reduced pressure and cooled to 5°. The product is collected and dried to give the title compound, m.p. 215.5°–218.5°.

Preparations 4 and 5

Following the general procedure of Preparation 3 and making non-critical variations but starting with the corresponding 16α-methyl or 16-hydrogen ($R_{16}$ is hydrogen) the following compounds are obtained.

Preparation 4: 17α,21-Dihydroxy-16α-methylpregna-1,4,9(11) triene-3,20-dione

Preparation 5: 17α,21-Dihydroxypregna-1,4,9(11)-triene-3,20-dione

Preparation 6: 17α,21-Dihydroxy-16β-methylpregna-1,4,9(11) triene-3,20-dione 17-propionate A mixture of 17α,21-dihydroxy-16β-methylpregna-1,4,9(11)-triene-3,20-dione (Preparation 3, 10 g.) in THF (220 ml.) containing triethylorthopropionate (11 ml.) and p-TSA (0.66 g.) is allowed to stand at 30° for 0.5 hours. Then sulfuric acid (2 N, 11 ml.) is added. The mixture is stirred for an additional 0.5 hours, made basic with potassium bicarbonate (1 N, 66 ml.), diluted with water and concentrated under reduced pressure. The precipitate is dissolved in methylene chloride, washed with aqueous potassium bicarbonate, dried and concentrated to give the title compound, TLC, Rf=0.40 (acetonemethylene chloride 10/90).

Preparations 7 and 8

Following the general procedure of Preparation 6 and making non-critical variations but starting with the 17,21-dihydroxy steroids of Preparations 4 and 5, (Column A) and 17-esters of Column B are obtained.

| Preparation | Column A | Column B |
|---|---|---|
| 7 | 4 | 17α,21-Dihydroxy-16α-methylpregna-1,4,9(11)-triene-3,20-dione 17-propionate |
| 8 | 5 | 17α,21-Dihydroxy-pregna-1,4,9(11)-triene-3,20-dione 17-propionate |

Preparation 9: 17α,21-Dihydroxy-16β-methylpregna-1,4,9(11)-triene-3,20-dione 17,21-dipropionate A mixture of 17α,21-Dihydroxy-16β-methylpregna-1,4,9(11)-diene-3,20-dione 17-propionate (Preparation 6, 4.1 g.) in pyridine (4 ml.) and propionic anhydride (8 ml.) is allowed to stand for 3 hours. The reaction mixture is diluted with ice water and acetone (100 ml.), allowed to stand for one hour and then concentrated under reduced pressure. The precipitate is collected, dissolved in SSB-ethyl acetate (4/1) and washed successively with aqueous potassium bisulfate, aqueous potassium bicarbonate and saline. The mixture is dried and concentrated under reduced pressure to a foam which is column chromatographed on silica gel (500 g.), packed in acetone-methylene chloride (5/95). Elution is performed with the same acetone-methylene chloride mixture. The appropriate fractions are pooled and concentrated to give the title compound, NMR (CDCl$_3$) 0.73, 1.16, 1.36, 1.40, 4.57, 5.6, 6.1–6.4 and 7.1–7.35 δ.

Preparations 10 and 11

Following the general procedure of Preparation 9 and making non-critical variations but starting with the 17-esters of Preparations 7 and 8 (Column C), the 17,23-diesters of Column D are obtained.

| Preparation | Column C | Column D |
|---|---|---|
| 10 | 7 | 17α,21 dihydroxy-16α-methylpregna-1,4,9(11)-triene-3,20-dione 17,21-dipropionate |
| 11 | 8 | 17α,21-dihydroxy-pregna-1,4,9(11)-triene-3,20-dione 17,21-dipropionate |

Preparation 12: 17α,21-Dihydroxy-16β-methylpregna-1,4,9(11)-triene-3,20-dione 17-propionate 21-mesylate A mixture of 17α,21-dihydroxy-16β-methylpregna-1,4,9(11)-triene-3,20-dione 17-propionate (Preparation 6, 8.3 g.) in pyridine (39 ml.) is cooled to 0° and methanesulfonylchloride (9.8 ml.) is added slowly. After stirring for one hour at 0°, the reaction mixture is poured into a mixture of ice water containing concentrated hydrochloric acid (30 ml.). The precipitate is collected, dissolved in methylene chloride and washed successively with aqueous potassium bisulfate, water and aqueous potassium bicarbonate. The mixture is dried and concentrated under reduced pressure to a foam which is column chromatographed on silica gel (1 kg.), packed in acetone-methylene chloride (5/95). Elution is performed in the same acetone-methylene chloride mixture, the appropriate fractions are pooled and concentrated to give the title compound. NMR (CDCl$_3$) 0.73, 1.16, 1.37, 1.41, 3.20, 4.7, 5.5, 6.0–6.4, and 7.1–7.3 δ.

Preparations 13 and 14

Following the general procedure of Preparation 12 and making non-critical variations but starting with and substituting the 21-hydroxy steroids of Preparations 7 and 8 (Column E), for 17α,21-dihydroxy-16β-methylpregna-1,4,9(11)-triene-3,20-dione 17-propionate, the 21-mesylates of Column F are obtained.

| Preparation | Column E | Column F |
|---|---|---|
| 13 | 7 | 17α,21-Dihydroxy-16α-methylpregna-1,4,9-(11)-triene-3,20-dione 17-propionate 21-mesylate |
| 14 | 8 | 17α,21-dihydro-5β-pregna-1,4,9(11)-triene-3,20-dione 17-propionate 21-mesylate |

Preparation 15: 17α,21-Dihydroxy-16β-methylpregna-4,9(11)-diene-3,20-dione

A mixture of 17α,21-dihydroxy-16β-methylpregna-4,9(11)-diene-3,20-dione 21-benzoate (U.S. Pat. No. 3,725,392, 32 g.) in methanol (700 ml.) is stirred with potassium carbonate (5.3 g.) in water (50 ml.) at 20°–25° for about 2 hours. The mixture is cooled, acidified with acetic acid (7 ml.), diluted with water (475 ml.) and concentrated under reduced pressure. The precipitate is collected, washed with water and dried to give the title compound, TLC, Rf=0.70 (acetone-methylene chloride, 20/80).

Preparation 16: 16β-Methyl-17α,20:20,21-bismethylenedioxypregna-4,9(11)dien-3-one A solution of hydrochloric acid (250 ml.) and formalin (35%, 250 ml.) prepared at 0° is added to a stirred suspension of 17α,21-dihydroxy-16β-methylpregna-4,9(11)-diene-3,20-dione (Preparation 15, 32 g.) in methylene chloride (900 ml.). The mixture is stirred for 16 hours at 20°–25° and diluted with ice water (500 ml.). The organic layer is separated, washed successively with cold aqueous sodium carbonate and water and then is dried and concentrated under reduced pressure. The residue is column chromatographed on silica gel packed in methylene chloride. Elution is performed with acetone-methylene chloride mixture beginning with 0% acetone and increasing to 7%. The appropriate fractions are pooled and concentrated to give a solid which is crystallized from acetone-SSB to give the title compound, m.p. 232.5°–237°; $[\alpha]_D$ −29°; UV $\lambda_{max}$=239.5 nm ($\epsilon$=17,250).

Preparation 17: 16β-Methyl-17α,20:20,21-bismethylenedioxy-5α-pregn-9(11)en-3-one A solution of 16β-methyl-17α,20:20,21-bismethylenedioxypregna-4,9(11)diene-3-one (Preparation 16, 22.8 g.) in THF (290 ml.) is added slowly (¾ hour) to a solution of lithium wire (2.28 g.) in liquid ammonia (1.1 l.) at −78°. The mixture is stirred for an additional one hour. Then ammonium chloride (17.7 g.) is added. The ammonia is allowed to evaporate on a steam bath and the mixture is concentrated under reduced pressure. The residue is stirred with acetone (600 ml.) and water (300 ml.), the pH is adjusted to 6 with hydrochloric acid and the mixture is further diluted with water (1.1 l.). The solid is collected, washed with water and dried at 60° under reduced pressure to give a solid which is recrystallized from aqueous acetone to give the title compound, m.p. 247°–255°; CMR 17.38 δ; IR (mull) 2770, 1712, 1673, 1691, 1078, 1007 and 946 cm$^{-1}$.

Preparation 18: 17α,21-Dihydroxy-16β-methyl-5α-pregn-9(11)-ene-3,20-dione

A suspension of 16β-methyl-17α,20:20,21-bismethylenedioxy-5α-pregn-9(11)-en-3-one (Preparation 17, 12.5 g.), acetic acid (375 ml.) and water (125 ml.) is heated under reflux for 2 hours. The mixture is then diluted with ice and water to 4 l. and stirred for about 20 minutes. The solid is collected, washed with water and suspended in acetone (750 ml.) and water (375 ml.). The mixture is neutralized with sodium hydroxide (1 N), diluted with ice water to 4 l., then refiltered. The product is collected and dried under reduced pressure to give the title compound TLC, Rf=0.18 (acetone-methylene chloride 10/90).

EXAMPLE 1

9α-Fluoro-11β,17α,21-trihydroxy-5β-pregnane-3,20-dione

9α-Fluoro-11β,17α,21-trihydroxy-5β-pregnane-3,20-dione 21 acetate (Preparation 1, 21.6 g.) in methanol (680 ml.) and aqueous potassium carbonate (10%, 75 ml.) is stirred for 0.5 hours under a nitrogen atmosphere. The mixture is then acidified with acetic acid (6 ml.), diluted with water and concentrated under reduced pressure. The mixture is cooled and the solid collected, dried and successively cyrstallized from aqueous acetone and acetone to give 9α-fluoro-11β,17α,21-trihydroxy-5β-pregnane-3,20-dione, m.p. 220°–228° (decomposition).

EXAMPLE 2

9α-Fluoro-11β,17α,21-trihydroxy-5β-pregnane-3,20-dione 17-propionate (I)

A mixture of 9α-fluoro-11β,17α,21-trihydroxy-5β-pregnane-3,20-dione (Example 1, 11.2 g.) in THF (230 ml.) containing triethylorthopropionate (11.6 ml.) and p-TSA (0.70 g.) is allowed to stand for 0.75 hours, then sulfuric acid (2 N, 11.6 ml.) is added, the mixture is stirred for an additional 0.3 hours, made basic with potassium bicarbonate (1 N, 70 ml.), diluted with water and concentrated under reduced pressure. The precipitate is dissolved in ethyl acetate, washed with saline, dried and concentrated to give 9α-fluoro-11β,17α,21-trihydroxy-5β-pregnane-3,20-dione 17-propionate, as a foam, TLC, Rf=0.29 (acetone-methylene chloride, 20/80).

EXAMPLES 3–6

Following the general procedure of Example 2, and making non-critical variations but substituting the ortho esters of Column G for triethylorthopropionate, the 17α-acyloxy-5β-steroids of Column H are obtained.

| Example | Column G | Column H |
|---|---|---|
| 3 | Trimethylorthoacetate | 9α-Fluoro-11β,17α,21-trihydroxy 5β-pregnane-3,20-dione 17-acetate |
| 4 | Triethylorthobutyrate | 9α-Fluoro-11β,17α,21-trihydroxy 5β-pregnane-3,20-dione 17-butyrate |
| 5 | Trimethylorthovalerate | 9α-Fluoro-11β,17α,21-trihydroxy 5β-pregnane-3,20-dione 17-valerate |
| 6 | Trimethylorthobenzoate | 9α-Fluoro-11β,17α,21-trihydroxy 5β-pregnane-3,20-dione 17-benzoate |

EXAMPLE 7

9α-Fluoro-11β,17α,21-trihydroxy-5β-pregnane-3,20-dione 17-propionate 21-mesylate (I)

A mixture of 9α-fluoro-11β,17α,21-trihydroxy-5β-pregnane-3,20-dione 17-propionate (Example 2, 11.0 g.) in pyridine (49 ml.) is cooled to 0° and methanesulfonyl chloride (12.2 ml.) is added over a period of 0.2 hours. After stirring for 1 hour at 0° the reaction mixture is poured into a mixture of ice and water containing concentrated hydrochloric acid (37.5 ml.). The precipitate is collected, dissolved in methylene chloride and washed successively with aqueous potassium bisulfate, water and aqueous potassium bicarbonate. The mixture is dried and concentrated under reduced pressure to a foam which is column chromatographed on silica gel (500 g.) packed in acetone-methylene chloride (5/95). Elution is performed with the same acetone-methylene chloride mixture. Appropriate fractions are pooled and concentrated to give 9α-fluoro-11β,17α,21-trihydroxy-5β-pregnane-3,20-dione 17-propionate 21-mesylate, NMR (CDCl$_3$) 4.91, 4.68–4.30, 3.18, 1.32, 1.15 and 0.95 δ.

EXAMPLES 8–11

Following the general procedures of Example 7 and making non-critical variations but starting with the 21-hydroxy compounds of Examples 3–6 (Column I) the 21-mesylates of Column J are obtained.

| Example | Column I | Column J |
|---|---|---|
| 8 | 3 | 9α-Fluoro-11β,17α,21-trihydroxy 5β-pregnane-3,20-dione 17-acetate 21-mesylate |
| 9 | 4 | 9α-Fluoro-11β,17α,21-trihydroxy 5β-pregnane-3,20-dione 17-butyrate 21-mesylate |
| 10 | 5 | 9α-Fluoro-11β,17α,21-trihydroxy-5β-pregnane-3,20-dione 17-valerate 21 mesylate |
| 11 | 6 | 9α-Fluoro-11β,17α,21-trihydroxy-5β-pregnane-3,20-dione 17-benzoate 21 mesylate |

EXAMPLE 12

21-Chloro-9α-fluoro-11β,17α-dihydroxy-5β-pregnane-3,20-dione 17-propionate (I)

A mixture of 9α-fluoro-11β,17α,21-trihydroxy-5β-prenane-3,20-dione 17-propionate 21-mesylate (Example 7, 8.4 g.) and lithium chloride (17.9 g.) in DMF (200 ml.) and acetone (330 ml.) is heated under reflux for 119 hours. The mixture is cooled and acetone is removed under reduced pressure. The mixture is then diluted with water and extracted with toluene. The organic extract is diluted with ethyl acetate, dried and concentrated under reduced pressure to give a foam which is crystallized from aqueous acetone and recrystallized from acetone-SSB to give the title compound, m.p. 191°–191.5° (decomposition); [α]$_D^{25}$+6°; IR (mull) 3420, 1740, 1730, 1695, 1275, 1215, 1205, 1095, 1050, 1035, and 1010 cm$^{-1}$; CMR 27.10 δ.

EXAMPLES 13–16

Following the general procedure of Example 12 and making non-critical variations but starting with the 21-mesylate compounds of Examples 8–11 (Column K) the 21-chloro steriods of Column L are obtained.

| Example | Column K | Column L |
|---|---|---|
| 13 | 8 | 21-Chloro-9α-fluoro-11β,17α-dihydroxy-5β-pregnane-3,20-dione 17-acetate |
| 14 | 9 | 21-Chloro-9α-fluoro-11β,17α-dihydroxy-5β-pregnane-3,20-dione 17-butyrate |
| 15 | 10 | 21-Chloro-9α-fluoro-11β,17α-dihydroxy-5β-pregnane-3,20-dione 17-valerate |
| 16 | 11 | 21-Chloro-9α-fluoro-11β,17α-dihydroxy-5β-pregnane-3,20-dione 17-benzoate |

EXAMPLE 17

21-Chloro-9α-fluoro-17α-hydroxy-5β-pregnane 3,11,20-trione 17-propionate (I)

21-Chloro-9α-fluoro-11β,17α-dihyroxy-5β-pregnane-3,20-dione 17-propionate (Example 12, 2.48 g.) is oxidized with Jones reagent following the general procedure of Example 64 and making non-critical variations. The reaction product is column chromatographed on silica gel (200 g.) packed in acetone-methylene chloride (5/95). Elution was performed with the same acetone-methylene chloride mixture. The appropriate fractions are pooled and concentrated to give a product which upon crystallization from acetone-SSB gives the title compound, m.p. 168.5°–169; [α]$_D^{25}$ −11°; IR (mull) 1730, 1710, 1270, 1190, 1180, 1170, and 1035 cm$^{-1}$.

EXAMPLES 18–21

Following the general procedure of Example 17 and making non-critical variations but starting with the 11-hydroxy steroid of Examples 13–16 (Column M) the 11-keto compounds of Column N are obtained.

| Example | Column M | Column N |
|---|---|---|
| 18 | 13 | 21-Chloro-9α-fluoro-17α-hydroxy 5β-pregnane-3,11,20-trione 17-acetate |
| 19 | 14 | 21-Chloro-9α-fluoro-17α-hydroxy 5β-pregnane-3,11,20-trione 17 butyrate |
| 20 | 15 | 21-Chloro-9α-fluoro-17α-hydroxy 5β-pregnane-3,11,20-trione 17-valerate |
| 21 | 16 | 21-Chloro-9α-fluoro-17α-hydroxy 5β-pregnane-3,11,20-trione 17-benzoate |

EXAMPLE 22

9α-Fluoro-11β,17α,21-trihydroxy-16β-methyl-5β pregnane-3,20-dione

9α-Fluoro-11β,17α,21-trihydroxy-16β-methyl-5β-pregnane-3,20-dione 21-benzoate (Preparation 2, 4.08 g.) in methanol (110 ml.) and aqueous potassium carbonate (10%, 12 ml.) is stirred for 1 hour under a nitrogen atmosphere. The mixture is then acidified with acetic acid (1 ml.), diluted with water (120 ml.) and extracted three times with SSB. The aqueous methanol phase is concentrated under reduced pressure. The mixture is cooled and the solid collected, dried and crystallized from acetone to give the title compound, m.p. 199°–205°; [α]$_D$ +78°; IR 3520, 3460, 3420, 1705, 1080, 1060 and 1050 cm$^{-1}$.

EXAMPLE 23

9α-Fluoro-11β,17α,21-trihydroxy-16β-methyl-5β-pregnane-3,20-dione 17-acetate (I)

A mixture of 9α-fluoro-11β,17α,21-trihydroxy-16β-methyl-5β-pregnane-3,20-dione (Example 22, 5.5 g.) in THF (110 ml.) containing trimethyl orthoacetate (5.5 ml.) and p-TSA (0.33 g.) is stirred for 0.75 hours, then sulfuric acid (2 N, 5.5 ml.) is added. The mixture is allowed to stand an additional 0.5 hours at 30°, then is cooled, made basic with potassium bicarbonate (1 N, 33 ml.), diluted with water and concentrated under reduced pressure. The precipitate is collected, dissolved in ethyl acetate, washed with saline, dried and concentrated to give the title compound, TLC, Rf=0.27 (methanol-methylene chloride, 5/95).

EXAMPLE 24

9α-Fluoro-11β,17α,21-trihydroxy-16β-methyl-5β-pregnane-3,20-dione 17-propionate (I)

9α-Fluoro-11β,17α,21-trihydroxy-16β-methyl-5β-pregnane-3,20-dione (Example 22, 1.23 g.) triethylorthopropionate (1.2 ml.) and p-TSA hydrate (0.072 g.) in THF (24 ml.) are allowed to stand at 30° for 0.5 hour under a nitrogen atmosphere. Aqueous sulfuric acid (1 N, 1.2 ml.) is then added and the mixture allowed to stand an additional 0.5 hour at 30°. The mixture is cooled to 5° and potassium bicarbonate (1 N, 7.2 ml.) and water (48 ml.) are added. The mixture is concentrated under reduced pressure, diluted with water and filtered. The filtrate is concentrated under reduced pressure to a gummy product which is column chromatographed on silica gel (150 g.), packed in acetone-methylene chloride (20/80). Elution is performed with the same solvent mixture. The appropriate fractions are pooled and concentrated. The concentrate is crystallized from acetone-hexane to give the title compound, m.p. 189° (decomposition); $[\alpha]_D$ +58°; IR 3480, 3420, 1730, 1695, 1225, 1180, 1165, 1085, 1065, 1035, 1010, 990, and 905 cm$^{-1}$.

EXAMPLES 25–27

Following the general procedure of Examples 23 and 24, and making non-critical variations but starting with the orthoesters of Column O, the 17-α-acyloxy-5β-steroids of Column P are obtained.

| Example | Column O | Column P |
|---|---|---|
| 25 | Triethyl orthobutyrate | 9α-Fluoro-11β,17α,21-trihydroxy-16β-methyl-5β-pregnane-3,20-dione 17 butyrate |
| 26 | Trimethyl orthovalerate | 9α-Fluoro-11β,17α,21-trihydroxy-16β-methyl-5β-pregnane-3,20-dione 17-valerate |
| 27 | Trimethyl orthobenzoate | 9α-Fluoro-11β,17α,21-trihydroxy-16β-methyl-5β-pregnane-3,20-dione 17-benzoate |

EXAMPLE 28

9α-Fluoro-11β,17α,21-trihydroxy-16β-methyl-5β-pregnane-3,20-dione 17-acetate 21-mesylate (I)

A solution of 9α-fluoro-11β,17α,21-trihydroxy-16β-methyl-5β-pregnane-3,20-dione 17-acetate (Example 23, 8.06 g.) in pyridine (27 ml.) is cooled to 5° and methane sulfonylchloride (6.7 ml) is slowly added. After stirring for one hour at 0°, the reaction mixture is poured into a mixture of ice and water containing concentrated hydrochloric acid (13.7 ml.). The precipitate is collected, redissolved in acetone (140 ml.) and potassium bicarbonate (1 N, 25 ml.) and allowed to stand one hour. The solution is concentrated under reduced pressure and extracted with methylene chloride. The extract is washed with saline, dried and concentrated to a foam which is column chromatographed on silica gel (300 g.). Elution is performed with acetone-methylene chloride (10/90). Appropriate fractions are pooled and concentrated under reduced pressure. The residue is crystallized from acetone-hexane to give the title compound, m.p. 154°–154.5°; NMR (CDCl$_3$) 0.95, 1.30, 1.35, 2.16, 3.21, 4.4 and 4.74 δ.

EXAMPLES 29–32

Following the general procedure of Example 28 and making non-critical variations but starting with the 21-hydroxy steroids of Examples 24–27 (Column Q) the 21-mesylate compounds of Column R are obtained.

| Example | Column Q | Column R |
|---|---|---|
| 29 | 24 | 9α-Fluoro-11β,17α,21-trihydroxy-16β-methyl-5β-pregnane-3,20-dione 17-propionate 21-mesylate |
| 30 | 25 | 9α-Fluoro-11β,17α,21-trihydroxy-16β-methyl-5β-pregnane-3,20-dione 17-butyrate 21-mesylate |
| 31 | 26 | 9α-Fluoro-11β,17α,21-trihydroxy-16β-methyl-5β-pregnane-3,20-dione 17-valerate 21-mesylate |
| 32 | 27 | 9α-Fluoro-11β,17α,21-trihydroxy-16β-methyl-5β-pregnane-3,20-dione 17-benzoate 21-mesylate |

EXAMPLE 33

21-Chloro-9α-fluoro-11β,17α-dihydroxy-16β-methyl-5β-pregnane-3,20-dione 17-acetate (I)

A mixture of 9α-fluoro-11β,17α,21-trihydroxy-16β-methyl-5β-pregnane-3,20-dione 17-acetate 21-mesylate (Example 28, 3 g.) in acetone (120 ml.) and DMF (74 ml.) containing lithium chloride (6.4 g.) is heated under reflux for six days and then cooled and poured into ice water. The precipitate is collected and dried, then is crystallized from acetone to give the title compound, m.p. 210.8°–211° (decomposition).

EXAMPLE 34

21-Chloro-9α-fluoro-11β,17α-dihydroxy-16β-methyl-5β-pregnane-3,20-dione 17-propionate (I)

Following the general procedure of Example 33 and making non-critical variations but starting with 9α-fluoro-11β,17α,21-trihydroxy-16β-methyl-5β-pregnane-3,20-dione 17-propionate 21-mesylate (Example 29) the title compound is obtained, m.p. 190°.

EXAMPLE 35

21-Chloro-9α-fluoro-11β,17α-dihydroxy-16β-methyl-5β-pregnane-3,20-dione 17-butyrate (I)

Following the general procedure of Example 33 and making non-critical variations but starting with 9α-fluoro-11β,17α,21-trihydroxy-16β-methyl-5β-pregnane-3,20-dione 17-butyrate 21-mesylate (Example 30), the title compound is obtained, m.p. 190°–192°.

EXAMPLE 36

21-Chloro-9α-fluoro-11β,17α-dihydroxy-16β-methyl-5β-pregnane-3,20-dione 17-valerate (I)

Following the general procedure of Example 33 and making non-critical variations but starting with 9α-fluoro-11β,17α,21-trihydroxy-16β-methyl-5β-pregnane-3,20-dione 17-valerate 21-mesylate (Example 31) the title compound is obtained, m.p. 173°–173.8°.

EXAMPLE 37

21-Chloro-9α-fluoro-11β,17α-dihydroxy-16-pregnane-3,20-dione 17-benzoate (I)

Following the general procedure of Example 33 and making non-critical variations but starting with 9α-fluoro-11β,17α,21-trihydroxy-16β-methyl-5β-pregnane-3,20-dione 17-benzoate 21-mesylate (Example 32) the title compound is obtained.

EXAMPLE 38

17α,21-Dihydroxy-16β-methyl-5β-pregn-9(11)-ene-3,20-dione 17,21-dipropionate

A mixture of 17α,21-dihydroxy-16β-methylpregna-1,4,9(11)-triene-3,20-dione 17,21-dipropionate (Preparation 9, 9.5 g.) in acetone (100 ml.) and triethylamine (16 ml.) is hydrogenated under two atmospheres of pressure in the presence of palladium on carbon (5%, 0.4 g.) for six hours. The mixture is filtered and the filtrate is condensed under reduced pressure to a foam which is column chromatographed on silica gel (300 g.) packed in acetone methylene chloride (2/98). Elution is performed with acetone-methylene chloride mixtures (2/98→5/95). The appropriate fractions are pooled and concentrated to give a product which upon crystallization from diethyl etherpentane gives the title compound, m.p. 120.5°-122°; IR (mull) 1740, 1730, 1280, 1220, 1210, 1180, 1070, 1050 and 1005 cm$^{-1}$; NMR (CDCl$_3$) 0.66, 1.14, 1.17, 1.19, 1.36, 4.6 and 5.6 δ.

EXAMPLES 39 AND 40

Following the general procedure of Example 38 and making non-critical variations but starting with the Δ$^{1,4}$ steroids of Preparations 10 and 11 (Column S), the 5β-steroids of Column T are obtained.

| Examples | Column S | Column T |
|---|---|---|
| 39 | 10 | 17α,21-Dihydroxy-16α-methyl-5β-pregn-9(11)-ene-3,20-dione 17,21-dipropionate |
| 40 | 11 | 17α,21-Dihydroxy-5β-pregn-9(11)-ene-3,20-dione 17,21-dipropionate |

EXAMPLE 41

9α,11β-Dichloro-17α,21-dihydroxy-16β-methyl-5β-pregnane-3,20-dione 17,21-dipropionate (I)

Following the general procedure of Example 50 and making non-critical variations but starting with 17α,21-dihydroxy-16β-methyl-5β-pregn-9(11)-ene-3,20-dione 17,21-dipropionate (I), the title compound is obtained.

EXAMPLES 42-43

Following the general procedure of Example 50 and making non-critical variations but starting with the Δ$^{9(11)}$ steroids of Examples 39-40 (Column U) the 9,11-dichloro steroids of Column V are obtained.

| Examples | Column U | Column V |
|---|---|---|
| 42 | 39 | 9α,11β-Dichloro-17α,21-dihydroxy 16α-methyl-5β-pregnane-3,20-dione 17,21-dipropionate |
| 43 | 40 | 9α,11β-Dichloro-17α,21-dihydroxy 5β-pregnene-3,20-dione 17,21-dipropionate |

EXAMPLE 44

17α,21-Dihydroxy-16β-methyl-5β-pregn-9(11)-ene-3,20-dione 17-propionate 21-mesylate A mixture of 17α,21-dihydroxy-16β-methylpregna-1,4,9(11)-triene-3,20-dione 17-propionate 21-mesylate (Preparation 12, 7.1 g.) in acetone (100 ml.) and triethylamine (2 ml.) is hydrogenated under two atmospheres of pressure in the presence of palladium on carbon (5%, 0.5 g.). The crude product obtained from hydrogenation is column chromatographed on silica gel (350 g.), packed in acetone-methylene chloride (2/98). Elution is performed with acetone-methylene chloride mixtures (2/8→5/95). The appropriate fractions are pooled and concentrated to give the title compound, NMR (CDCl$_3$) 0.67, 1.14, 1.19, 1.37, 3.20, 4.72 and 5.6 δ.

EXAMPLE 45 AND 46

Following the general procedure of Example 44 and making non-critical variations but starting with and substituting the Δ$^{1,4}$-steroids of Preparations 13 and 14 (Column W) for 17α,21-dihydroxy-16β-methylpregna-1,4,9(11)-triene-3,20-dione 17-propionate 21-mesylate, the 5β-steroids of Column X are obtained.

| Example | Column W | Column X |
|---|---|---|
| 45 | 13 | 17α,21-Dihydroxy-16α-methyl-5β-pregna-9(11)-ene-3,20-dione 17-propionate 21-mesylate |
| 46 | 14 | 17α,21-Dihydroxy-5β-pregna-9(11)-ene-3,20-dione 17-propionate 21-mesylate |

EXAMPLE 47

21-Chloro-17α-hydroxy-16β-methyl-5β-pregn-9(11)-ene-3,20-dione 17-propionate

17α,21-Dihydroxy-16β-methyl-5β-pregn-9(11)-ene-3,20-dione 17-propionate 21-mesylate (Example 44, 7.69 g.) in acetone (320 ml.) and DMF (200 ml.) are heated under reflux with lithium chloride (17.1 g.) for 90 hours. The mixture is then concentrated under reduced pressure, diluted with ice water and filtered. The filter cake is dissolved in methylene chloride, washed with saline and the methylene chloride mixture is dried and concentrated under reduced pressure to a foam which is crystallized from acetone-pentane to give the title compound, m.p. 140.5°-141.5°; IR (mull) 3040, 1745, 1735, 1710, 1645, 1355, 1205, 1195, 1040, 1015, 965 and 710 cm$^{-1}$; [α]$_D$ +54°.

EXAMPLES 48 AND 49

Following the general procedure of Example 47 and making non-critical variations but starting with and substituting the 5β-steroids of Examples 45 and 46 (Column Y) for 17α,21-dihydroxy-16β-methyl-5β-pregn-9(11)-ene-3,20-dione 17-propionate 21-mesylate, the 21-chloro steroids of Column Z are obtained.

| Example | Column Y | Column Z |
|---|---|---|
| 48 | 45 | 21-Chloro-17α-hydroxy-16α-methyl-5β-pregn-9(11)-ene-3,20-dione 17-propionate |
| 49 | 46 | 21-Chloro-17α-hydroxy-5β-pregn-9(11)-ene-3,20-dione 17-propionate |

EXAMPLE 50

9α,11β,21-Trichloro-17α-hydroxy-16β-methyl-5β-pregnane-3,20-dione 17-propionate (I)

A mixture of 21-chloro-17α-hydroxy-16β-methyl-5β-pregn-9(11)-ene-3,20-dione 17-propionate (Example 47, 1.3 g.) in chloroform (100 ml.) and pyridine (1 ml.) is cooled to −10°. A chlorine solution in carbon tetrachloride (40 ml., 1.15 eq.) is added at −10° and the reaction mixture is washed successively with cold aqueous potassium bisulfate, water and cold aqueous potassium bicarbonate. The layers are separated and the organic layer is concentrated under reduced pressure to a foam which is crystallized from diethyl ether-pentane and recrystallized from acetone-hexane to give the title compound, m.p. 163.8°–164°; NMR (CDCl$_3$) 1.01, 1.19, 1.38, 1.57, 3.98 and 4.7–4.8 δ.

EXAMPLES 51 AND 52

Following the general procedure of Example 50 and making non-critical variations but starting with the Δ$^{9(11)}$-steroids of Examples 48 and 49, (Column AA) the 21-chloro steroids of Column BB are obtained.

| Example | Column AA | Column BB |
|---|---|---|
| 51 | 48 | 9α,11β,21-Trichloro-17α-hydroxy-16α-methyl-5β-pregnane-3,20-dione 17-propionate |
| 52 | 49 | 9α,11β,21-Trichloro-17α-hydroxy-5β-pregnane-3,20-dione 17-propionate |

EXAMPLE 53

21-Chloro-9α-fluoro-11β,17α-dihydroxy-16β-methyl-5β-pregnane-3,20-dione 17-propionate (I)

A mixture of 21-chloro-9α-fluoro-11β,17α-dihydroxy-16β-methylpregna-1,4-diene-3,20-dione 17-propionate (IA, U.S. Pat. No. 3,721,687, Example 14, 2.0 g.) in ethyl acetate is stirred with palladium on carbon (2 g.) under one atmosphere of hydrogen for 2 hours and then filtered thru diatomaceous earth. The filtrate is concentrated under reduced pressure. The concentrate is column chromatographed over silica gel (200 g.) packed in acetone-methylene chloride (5/95). Elution is performed with the same solvent mixture. The appropriate fractions (TLC) are pooled and concentrated to a solid. Upon crystallization from acetone-SSB the title compound is obtained, m.p. 191°; IR (mull) 3360, 1725, 1685, 1285, 1225, 1205, 1060, 1040, 1010, 990, 905 and 695 cm$^{-1}$; CMR 27.05 δ and [α]$_D$ +63°.

EXAMPLE 54–63

Following the general procedure of Example 1 and making non-critical variations but starting with the Δ$^{1,4}$-steroids (U.S. Pat. No. 3,731,687) of Column CC, the 5β-steriods of Column DD are obtained.

| Example | Column CC | Column DD |
|---|---|---|
| 54 | 9α,21-Difluoro-11β,17α-dihydroxy-16β-methylpregna-1,4-diene-3,20-dione 17-acetate | 9α,21-Difluoro-11β,17α-dihydroxy-16β-methyl-5β-pregnane-3,20-dione 17-acetate |
| 55 | 9α,21-Difluoro-11β,17α-dihydroxy-16β-methylpregna-1,4-diene-3,20-dione 17-propionate | 9α21-Difluoro-11β,17α-dihydroxy-16β-methyl-5β-pregnane-3,20-dione 17-propionate |
| 56 | 9α,21-Difluoro-11β,17α-dihydroxy-16β-methylpregna-1,4-diene-3,20-dione 17-butyrate | 9α21-Difluoro-11β,17α-dihydroxy-16β-methyl-5β-pregnane-3,20-dione 17-butyrate |
| 57 | 9α,21-Difluoro-11β,17α-dihydroxy-16β-methylpregna-1,4-diene-3,20-dione 17-isobutyrate | 9α,21-Difluoro-11β,17α-dihydroxy-16β-methyl-5β-pregnane-3,20-dione 17-isobutyrate |
| 58 | 9α,21-Difluoro-11β,17α-dihydroxy-16β-methylpregna-1,4-diene-3,20-dione 17-valerate | 9α,21-Difluoro-11β,17α-dihydroxy-16β-methyl-5β-pregnane-3,20-dione 17-valerate |
| 59 | 21-Chloro-9α-fluoro-11β,17α-dihydroxy-16β-methylpregna-1,4-diene-3,20-dione 17-acetate | 21-Chloro-9α-fluoro-11β,17α-dihydroxy-16β-methyl-5β-pregnane-3,20-dione 17-acetate |
| 60 | 21-Chloro-9α-fluoro-11β,17α-dihydroxy-16β-methylpregna-1,4-diene-3,20-dione 17-butyrate | 21-Chloro-9α-fluoro-11β,17α-dihydroxy-16β-methyl-5β-pregnane-3,20-dione 17-butyrate |
| 61 | 21-Chloro-9α-fluoro-11β,17α-dihydroxy-16β-methylpregna-1,4-diene-3,20-dione 17-isobutyrate | 21-Chloro-9α-fluoro-11β,17α-dihydroxy-16β-methyl-5β-pregnane-3,20-dione 17-isobutyrate |
| 62 | 21-Chloro-9α-fluoro-11β,17α-dihydroxy-16β-methylpregna-1,4-diene-3,20-dione 17-valerate | 21-Chloro-9α-fluoro-11β,17α-dihydroxy-16β-methyl-5β-pregnane-3,20-dione 17-valerate |
| 63 | 21-Chloro-9α-fluoro-11β,17α-dihydroxy-16β-methylpregna-1,4-diene-3,20-dione 17-benzoate | 21-Chloro-9α-fluoro-11β,17α-dihydroxy-16β-methyl-5β-pregnane-3,20-dione 17-benzoate |

EXAMPLE 64

21-Chloro-9α-fluoro-17α-hydroxy-16β-methyl-5β-pregnane-3,11,20-trione 17-propionate (I)

Jones reagent (chromium trioxide-aqueous sulfuric acid, 1.3 ml.) is added to a solution of 21-chloro-9α-fluoro-11β,17α-dihydroxy-16β-methyl-5β-pregnane-3,20-dione 17-propionate (Example 53, 2 g.) in acetone (50 ml). The mixture is stirred for 30 minutes at 20°–25°. Isopropyl alcohol (1.3 ml.) is added followed by slow addition of ice water (600 ml.). The precipitate is collected, washed with water and dried. The crude product is column chromatographed on silica gel eluting with acetone-methylene chloride (5/95). The appropriate fractions (TLC) are pooled, concentrated under reduced pressure and crystallized from acetone-SSB to give the title compound, m.p. 184°–185.5°; IR 1730, 1275, 1260, 1185, 1170, 1040 and 960 cm$^{-1}$; CMR 24.38 δ and [α]$_D$ +42°.

EXAMPLE 65

21-Chloro-9α-fluoro-17α-hydroxy-16β-methyl-5β-pregnane-3,11,20-trione 17-butyrate (I)

Following the general procedure of Example 64 and making non-critical variations but starting with 21-chloro-9α-fluoro-11β,17α-dihydroxy-16β-methyl-5β-pregnane-3,20-dione 17-butyrate there is obtained the title compound.

EXAMPLE 66

9α-Fluoro-11β,17α-dihydroxy-16β-methyl-5β-pregnane-3,20-dione 17-propionate

21-Chloro-9α-fluoro-11β,17α-dihydroxy-16β-methyl-5β-pregnane-3,20-dione 17-propionate (I, Example 53, 4.0 g.) in acetone (100 ml.) containing triethylamine (2 ml.) is hydrogenated in the presence of palladium on carbon (5%, 0.42 g.) until the uptake of hydrogen is complete. The mixture is filtered and the filtrate is concentrated under reduced pressure. The concentrate is column chromatographed on silica gel (200 g.) packed in acetone-methylene chloride (5/95) and eluted with the same mixture. The appropriate fractions (TLC) are pooled and concentrated to a solid. Upon crystallization from acetone-SSB the title compound is obtained, m.p. 176°–178°; $[\alpha]_D^{25}$ 43°; CMF (CDCl$_3$) 27.12 δ and IR (mull) 3481, 1722, 1702, 1294, 1227, 1205, 1067, 1058, 1043, 1004, 988, and 953 cm$^{-1}$.

EXAMPLES 67–72

Following the general procedure of Example 66 and making non-critical variations but starting with the 21-chloro steroid of Examples 53 and 59–63 (Column EE), the compounds of Column FF are obtained.

| Example | Column EE | Column FF |
|---|---|---|
| 67 | 53 | 9α-Fluoro-11β,17α-dihydroxy-16β-methyl-5β-pregnane-3,20-dione 17-propionate |
| 68 | 59 | 9α-Fluoro-11β,17α-dihydroxy-16β-methyl-5β-pregnane-3,20-dione 17-acetate |
| 69 | 60 | 9α-Fluoro-11β,17α-dihydroxy-16β-methyl-5β-pregnane-3,20-dione 17-butyrate |
| 70 | 61 | 9α-Fluoro-11β,17α-dihydroxy-16β-methyl-5β-pregnane-3,20-dione 17-isobutyrate |
| 71 | 62 | 9α-Fluoro-11β,17α-dihydroxy-16β-methyl-5β-pregnane-3,20-dione 17-valerate |
| 72 | 63 | 9α-Fluoro-11β,17α-dihydroxy-16β-methyl-5β-pregnane-3,20-dione 17-benzoate |

EXAMPLE 73

21-Chloro-9α-fluoro-11β,17α-dihydroxy-16β-methyl-5β-pregnane-3,20-dione 17-benzoate (I)

21-Chloro-9α-fluoro-11α,17α-dihydroxy-16β-methylpregna-1,4-diene-3,20-dione 17-benzoate (IA, 3.9 g.) in ethyl acetate (375 ml.) is stirred with palladium on carbon (5%, 1 g.) under one atmosphere of hydrogen until the uptake of hydrogen is complete. The mixture is then filtered and the filtrate is concentrated under reduced pressure to a solid which is column chromatographed on silica gel (400 g.) packed in methanol-methylene chloride (2/98). Elution is performed with the same methanol-methylene chloride mixture to give the product which upon crystallization from acetone-SSB gives the title compound, m.p. 174.5°–175.5° (decomposition); CMR (CDCl$_3$) 27.18 δ; IR (mull) 3440, 1735, 1715, 1695, 1600, 1580, 1490, 1275, 1260, 1105, 990, and 720 cm$^{-1}$.

EXAMPLE 74

9α-Fluoro-11β,17α,21-trihydroxy-16β-methyl-5β-pregnane-3,20-dione 17,21-dipropionate (I)

9α-Fluoro-11β,17α,21-trihydroxy-16β-methylpregn-4-ene-3,20-dione 17,21-dipropionate (IA, 4.75 g.) in ethyl acetate (260 ml.) is stirred with palladium on carbon (5%, 2.1 g.) under hydrogen (1 atmosphere) until the uptake of hydrogen is complete. The mixture is filtered and the filtrate is concentrated under reduced pressure to a solid which is column chromatographed on silica gel (400 g.) packed in acetone-methylene chloride (5/95). Elution is performed with the same acetone-methylene chloride mixture. The appropriate fractions (TLC) are pooled and concentrated to a solid. Upon crystallization from acetone-SSB the title compound is obtained, m.p. 143°–144°; $[\alpha]_D$ +36°; CMR (CDCl$_3$) 27.0 δ and IR (mull) 3460, 1750, 1735, 1720, 1710, 1195, 1180, 1165, 1090, 1070, 1045, 1020, 990, 995 and 810 cm$^{-1}$.

EXAMPLE 75

9α-Fluoro-11β,17α,21-trihydroxy-16β-methyl-5β-pregnane-3,20-dione 17,21-dipropionate (I)

9α-Fluoro-11β,17α,21-trihydroxy-16β-methylpregna-1,4-diene-3,20-dione 17,21-dipropionate (IA, betamethasone 17,21-dipropionate, 1.0 g.) and p-TSA hydrate (0.1 g.) in acetone (100 ml.) are shaken with palladium on carbon (5%, 0.1 g.) under hydrogen (2 atmospheres) until the uptake of hydrogen is complete. The mixture is filtered and the filtrate is concentrated under reduced pressure. The residue is dissolved in methylene chloride, washed with aqueous sodium bicarbonate and dried. The mixture is concentrated and the residue is column chromatographed over silica gel (100 g.) packed in acetone-methylene chloride (10/90). Elution is performed with the same solvent mixture. The appropriate fractions are pooled and concentrated. Upon crystallizaton from acetone-hexane the title compound is obtained, m.p. 142°–143.5°.

EXAMPLE 76

9α-Fluoro-11β,17α,21-trihydroxy-16β-methyl-5β-pregnane-3,20-dione 17-propionate 21-mesylate (I)

9α-Fluoro-11β,17α,21-trihydroxy-16β-methylpregna-1,4-diene-3,20-dione 17-propionate 21-mesylate (IA, U.S. Pat. No. 3,721,687, Example 1, 5.0 g.) in acetone (100 ml.) is hydrogenated in the presence of palladium on carbon (5%, 0.5 g.) and p-TSA (0.10 g.) until the uptake of hydrogen is complete. The mixture is filtered and the filtrate is concentrated under reduced pressure. The concentrate is chromatographed on silica gel (250 g.) packed in acetone-methylene chloride (5/95). Elution is performed on the same mixture. The appropriate fractions (TLC) are pooled and concentrated to give a solid. An acetone solution of the foam is slowly added to water to give an amorphous precipitate which is collected and dried to give the title compound, m.p. 109°–115°; $[\alpha]_D^{25}$ +44°; CMF (CDCl$_3$) 27.07 δ and IR (mull) 3544, 3464, 1736, 1706, 1356, 1177, 1041, 1013, 987, 952, 926 and 812 cm$^{-1}$.

EXAMPLE 77

21-Bromo-9α-fluoro-11β,17α-dihydroxy-16β-methyl-5β-pregnane-3,20-dione 17-propionate (I)

A mixture of 9α-fluoro-11β,17α,21-trihydroxy-16β-methyl-5β-pregnane-3,20-dione 17-propionate 21-mesylate (Example 76, 2.0 g.), lithium bromide (4 g.), acetone (80 ml.) and DMF (50 ml.) is heated under reflux for 70 hours. The reaction mixture is concentrated under reduced pressure and the concentrate is poured into ice water. A precipitate is collected, dried and then column chromatographed on silica gel (300 g.) and eluted with acetone-methylene chloride (5/95). The appropriate fractions (TLC) are pooled and concentrated to a solid. Upon crystallization from acetone-SSB the title compound is obtained, m.p. 184.5° (decomposition); $[\alpha]_D^{25}$ +64°; CMR (CDCl$_3$) 27.14 δ and IR (mull) 3353, 1725, 1689, 1284, 1244, 1206, 1088, 1062, 1014, 1012, 990 and 905 cm$^{-1}$.

EXAMPLE 78

21-Chloro-9α-fluoro-11β,17α-dihydroxy-6α-methyl-5β-pregnane-3,20-dione 17-valerate (I)

21-Chloro-9α-fluoro-11β,17α-dihydroxy-6α-methylpregna-1,4-diene-3,20-dione 17-valerate (IA, 0.6 g.) in acetone (100 ml.) is hydrogenated in the presence of palladium on carbon (5%, 0.1 g.) until the uptake of hydrogen is complete. The mixture is filtered and the filtrate concentrated under reduced pressure. The concentrate is column chromatographed on silica gel (50 g.) packed in methylene chloride. Elution is performed with acetone-methylene chloride mixtures. The appropriate fractions are pooled and concentrated to give a solid which upon crystallization from acetone-SSB gives the title compound, m.p. 168°–169°; $[\alpha]_D^{25}$ −11°; CMR (CDCl$_3$) 27.48 δ; IR (mull) 3540, 3400, 1735, 1725, 1720, 1695, 1265, 1240, 1185, and 980 cm$^{-1}$.

EXAMPLE 79

9α-Fluoro-11β,17α-dihydroxy-6α-methyl-5β-pregnane-3,20-dione 17-acetate (I)

Following the general procedure of Example 78 and making non-critical variations but starting with 9α-fluoro-11β,17α-dihydroxy-6α-methylpregna-1,4-diene-3,20-dione 17-acetate the title compound is obtained.

EXAMPLE 80

21-Chloro-9α-fluoro-17α-hydroxy-6α-methyl-5β-pregnane-3,11,20-trione 17-valerate (I)

21-Chloro-9α-fluoro-17α-hydroxy-6α-methylpregna-1,4-diene-3,11,20-trione 17-valerate (IA, 1.15 g.) is hydrogenated following the general procedure of Example 78 and making non-critical variations, the title compound is obtained as an amorphous solid, m.p. 67°–72°; $[\alpha]_D^{25}$ −27°; CMR 24.71 δ; IR (mull) 1725, 1270, 1235, 1160, 1110, 1095, and 1030 cm$^{-1}$.

EXAMPLE 81

6α,9α-Difluoro-11β,17α,21-trihydroxy-16β-methyl-5β-pregnane-3,20-dione 17,21-diacetate (I)

Following the general procedure of Example 78 and making non-critical variations but starting with 6α,9α-difluoro-11β,17α,21-trihydroxy-16β-methylpregna-1,4-diene-3,20-dione 17,21-diacetate (IA, U.S. Pat. No. 3,980,778, 7.82 g.) the title compound is obtained upon crystallization from acetone-SSB and recrystallization from acetone, m.p. 225° (decomposition); $[\alpha]_D^{25}$ +28°; CMR 27.24 δ; IR (mull) 3540, 1745, 1735, 1710, 1245, 1210, 1025, 1010, 1000 and 960 cm$^{-1}$.

EXAMPLES 82–84

Following the general procedure of Example 81 and making non-critical variations but starting with the Δ$^{1,4}$-steroids of Column DD (U.S. Pat. No. 3,780,177) the corresponding 5β-steroids (I) of Column EE are obtained.

| Example | Column DD | Column EE |
| --- | --- | --- |
| 82 | 6α,9α-Difluoro-11β,17α,21-trihydroxypregna-1,4-diene-3,20-dione 17-butyrate 21-acetate | 6α,9α-Difluoro-11β,17α,21-trihydroxy-5β-pregnane-3,20-dione 17-butyrate 21-acetate |
| 83 | 6α,9α-Difluoro-11β,17α,21-trihydroxypregna-1,4-diene-3,20-dione 17-butyrate 21-propionate | 6α,9α-Difluoro-11β,17α,21-trihydroxy-5β-pregnane-3,20-dione 17-butyrate 21-propionate |
| 84 | 6α,9α-Difluoro-11β,17α,21-trihydroxypregna-1,4-diene-3,20-dione 17,21-dibutyrate | 6α,9α-Difluoro-11β,17α,21-trihydroxy-5β-pregnane-3,20-dione 17,21-dibutyrate |

EXAMPLE 85

6α,9α-Difluoro-17α,21-dihydroxy-16β-methyl-5β-pregnane-3,11,20-trione 17,21-diacetate (I)

Following the general procedure of Example 64 and making non-critical variations and starting with 6α,9α-difluoro-11β,17α,21-trihydroxy-16β-methyl-5β-pregnane-3,20-dione 17,21-diacetate (Example 81, 5 g.) the title compound is obtained, upon crystallization from acetone-SSB, m.p. 251.5°; $[\alpha]_D^{25}$ +1°; CMR (CDCl$_3$) 24.68 δ; IR (mull) 1755, 1735, 1715, 1240, 1205, 1070, 1045, and 1015 cm$^{-1}$.

EXAMPLES 86–88

Following the general procedure of Example 85 and making non-critical variations but starting with the steroids of Examples 82–84, (Column GG) the 11-keto steroids of Column HH are obtained.

| Example | Column GG | Column HH |
| --- | --- | --- |
| 86 | 82 | 6α,9α-Difluoro-17α,21-dihydroxy-5β-pregnane-3,11,20 trione 17-butyrate 21-acetate |
| 87 | 83 | 6α,9α-Difluoro-17α,21-dihydroxy-5β-pregnane-3,11,20 trione 17-butyrate 21-propionate |
| 88 | 84 | 6α,9α-Difluoro-17α,21-dihydroxy-5β-pregnane-3,11,20 trione 17,21-dibutyrate |

EXAMPLE 89

9α-Fluoro-11β,17α,21-trihydroxy-16β-methyl-5β-pregnane-3,20-dione 17-valerate (I)

9α-Fluoro-11β,17α,21-trihydroxy-16β-methylpregna-1,4-diene-3,20-dione 17-valerate (IA, betamethasone 17-valerate, 3.0 g.) and triethylamine (1.5 ml.) in acetone (100 ml.) are shaken with palladium on carbon (5%, 0.3 g.) under hydrogen (2 atmospheres) until the uptake of hydrogen is complete. The mixture is filtered and the filtrated concentrated under reduced pressure. The residue is column chromatographed on silica gel (300 g.) packed in acetone-methylene chloride (10–90). Elution is performed with the same solvent mixture. The appropriate fractions are pooled and concentrated. Upon crystallizing the residue from ether-pentane the title compound is obtained, m.p. 135°–136°; IR 3480, 3440, 1725, 1710, 1295, 1260, 1180, 1090, 1065, 1040, 1015, 985 and 950 cm$^{-1}$.

EXAMPLES 90–103

Following the general procedure of Example 89 and making non-critical variations but starting with the Δ$^{1,4}$-steroids of Column II, the 5β-steriods of Column JJ are obtained.

| Example | Column II | Column JJ |
|---|---|---|
| 90 | 9α-Fluoro-11β,17α,21-trihydroxy-16β-methylpregna-1,4-diene-3,20-dione 17-acetate | 9α-Fluoro-11β,17α,21-trihydroxy-16β-methyl-5β-pregnane-3,20-dione 17-acetate |
| 91 | 9α-Fluoro-11β,17α,21-trihydroxy-16β-methylpregna-1,4-diene-3,20-dione 17-propionate | 9α-Fluoro-11β,17α,21-trihydroxy-16β-methyl-5β-pregnane-3,20-dione 17-propionate |
| 92 | 9α-Fluoro-11β,17α,21-trihydroxy-16β-methylpregna-1,4-diene-3,20-dione 17-butyrate | 9α-Fluoro-11β,17α,21-trihydroxy-16β-methyl-5β-pregnane-3,20-dione 17-butyrate |
| 93 | 9α-Fluoro-11β,17α,21-trihydroxy-16β-methylpregna-1,4-diene-3,20-dione 17-benzoate | 9α-Fluoro-11β,17α,21-trihydroxy-16β-methyl-5β-pregnane-3,20-dione 17-benzoate |
| 94 | 9α-Fluoro-11β,17α,21-trihydroxy-16α-methylpregna-1,4-diene-3,20-dione-17 acetate | 9α-Fluoro-11β,17α,21-trihydroxy-16α-methyl-5β-pregnane-3,20-dione 17-acetate |
| 95 | 9α-Fluoro-11β,17α,21-trihydroxy-16α-methylpregna-1,4-diene-3,20-dione 17-propionate | 9α-Fluoro-11β,17α,21-trihydroxy-16α-methyl-5β-pregnane-3,20-dione 17-propionate |
| 96 | 9α-Fluoro-11β,17α,21-trihydroxy-16α-methylpregna 1,4-diene-3,20-dione 17-butyrate | 9α-Fluoro-11β,17α,21-trihydroxy-16α-methyl-5β-pregnane-3,20-dione 17-butyrate |
| 97 | 9α-Fluoro-11β,17α,21-trihydroxy-16α-methylpregan-1,4-diene-3,20-dione 17-valerate | 9α-Fluoro-11β,17α,21-trihydroxy-16α-methyl-5β-pregnane-3,20-dione 17-valerate |
| 98 | 9α-Fluoro-11β,17α,21-trihydroxy-16α-methylpregna-1,4-diene-3,20-dione 17-benzoate | 9α-Fluoro-11β,17α,21-trihydroxy-16α-methyl-5β-pregnane-3,20-dione 17-benzoate |
| 99 | 9α-Fluoro-11β,17α,21-trihydroxypregna-1,4-diene-3,20-dione 17-acetate | 9α-Fluoro-11β,17α,21-trihydroxy-5β-pregnane-3,20-dione 17-acetate |
| 100 | 9α-Fluoro-11β,17α,21-trihydroxypregna-1,4-diene-3,20-dione 17-propionate | 9α-Fluoro-11β,17α,21-trihydroxy-5β-pregnane-3,20-dione 17-propionate |
| 101 | 9α-Fluoro-11β,17α,21-trihydroxypregna-1,4-diene-3,20-dione 17-butyrate | 9α-Fluoro-11β,17α,21-trihydroxy-5β-pregnane-3,20-dione 17-butyrate |
| 102 | 9α-Fluoro-11β,17α,21-trihydroxypregna-1,4-diene-3,20-dione 17-valerate | 9α-Fluoro-11β,17α,21-trihydroxy-5β-pregnane-3,20-dione 17-valerate |
| 103 | 9α-Fluoro-11β,17α,21-trihydroxypregna-1,4-diene-3,20-dione 17-benzoate | 9α-Fluoro-11β,17α,21-trihydroxy-5β-pregnane-3,20-dione 17-benzoate |

EXAMPLE 104

9α-Fluoro-11β,17α,21-trihydroxy-16α-methyl-5β-pregnane-3,20-dione 17-propionate 21-mesylate (I)

A mixture of 9α-fluoro-11β,17α,21-trihydroxy-16α-methylpregna-1,4-diene-3,20-dione 17-propionate 21-mesylate (IA, dexamethasone 17-propionate 21-mesylate, U.S. Pat. No. 3,721,687, Example 5, 3.6 g.), triethylamine (1.5 ml.) and acetone (100 ml.) are shaken with palladium on carbon (5%, 0.3 g.) under hydrogen (2 atmospheres) until the uptake of hydrogen is complete. The mixture is filtered and the filtrate concentrated under reduced pressure. The residue is column chromatographed on silica gel (200 g.), packed in methanol-methylene chloride (2/98). Elution is performed in the same solvent mixture. The appropriate fractions are pooled and concentrated to give the title compound; NMR (CDCl₃) 0.90, 1.0, 1.16, 1.29, 3.2, 4,4, 4.84δ.

EXAMPLE 105

21-Bromo-9α-fluoro-11β,17α-dihydroxy-16α-methyl-5β-pregnane-3,20-dione 17-propionate (I)

A mixture of 9α-fluoro-11β,17α,21-trihydroxy-16α-methyl-5β-pregnane-3,20-dione 17-propionate 21-mesylate (Example 104, 3.6 g.) and lithium bromide (fused, 7.2 g.) in acetone (144 ml.) and DMF (90 ml.) are heated under reflux for 10 days. The mixture is then concentrated under reduced pressure, diluted with water and filtered to obtain the precipitate. The solid is chromatographed on silica gel (360 g.) packed in acetone-methylene chloride (5/95) and eluted with the same solvent mixture. The appropriate fractions are pooled and concentrated. The concentrate is rechromatographed on silica gel using acetone-methylene chloride (2/98) as the eluant. The appropriate fractions are pooled and concentrated. Upon crystallization from acetone the title compound is obtained, m.p. 178°–178.5° (decomposition); $[\alpha]_D + 22°$.

EXAMPLE 106

9α-Fluoro-11β,17α-dihydroxy-16α-methyl-5β-pregnane-3,20-dione 17-propionate (I)

21-Bromo-9α-fluoro-11β,17α-dihydroxy-16α-methyl-5β-pregnane-3,20-dione 17-propionate (I, Example 105, 1.6 g.) in acetone (100 ml.) containing triethylene (1 ml.) is hydrogenated in the presence of palladium on carbon (5%, 0.1 g.) and worked up in the usual manner. Crystallization of the chromatographed product from acetone gives the title compound, m.p. 144.5–147.5° (decomposition); $[\alpha]_D + 12°$.

EXAMPLE 107

21-Chloro-9α-fluoro-11β,17α-dihydroxy-16α-methyl-5β-pregnane-3,20-dione 17-propionate (I)

21-Chloro-9α-fluoro-11β,17α-dihydroxy-16α-methylpregna-1,4-diene-3,20-dione 17-propionate (IA, U.S. Pat. No. 3,721,687, Example 20, 1.67 g.) in acetone (100 ml.) is hydrogenated in the presence of p-TSA hydrate (0.18 g.) and palladium on carbon (5%, 0.18 g.) until the uptake of hydrogen is complete. The mixture is filtered and the filtrate is concentrated under reduced pressure. The crude product is dissolved in acetone and precipitated by the addition of water to give a solid which is obtained by filtration. Crystallization of the solid from acetone gives the title compound, m.p. 198° (decomposition); CMR 27.1δ; $[\alpha]_D + 14$; IR 3360, 1715, 1680, 1290, 1240, 1200, 1085, 1045, 1020, 1010 and 905 cm⁻¹.

EXAMPLES 108–111

Following the general procedure of Example 107 and making non-critical variations but starting with the Δ¹,⁴-steriods of Column KK, the 5β-steriods of Column LL are obtained.

| Example | Column KK | Column LL |
|---|---|---|
| 108 | 21-Chloro-9α-fluoro-11β,17α-dihydroxy-16α-methylpregna-1,4-diene-3,20-dione 17-acetate | 21-Chloro-9α-fluoro-11β,17α-dihydroxy-16α-methyl-5β-pregnane-3,20-dione 17-acetate |
| 109 | 21-Chloro-9α-fluoro-11β,17α-dihydroxy-16α-methylpregna-1,4-diene-3,20-dione 17-butyrate | 21-Chloro-9α-fluoro-11β,17α-dihydroxy-16α-methyl-5β-pregnane-3,20-dione 17-butyrate |

| Example | Column KK | Column LL |
|---|---|---|
| 110 | 21-Chloro-9α-fluoro-11β,17α-dihydroxy-16α-methylpregna-1,4-diene-3,20-dione 17-valerate | 21-Chloro-9α-fluoro-11β,17α-dihydroxy-16α-methyl-5β-pregnane-3,20-dione 17-valerate |
| 111 | 21-Chloro-9α-fluoro-11β,17α-dihydroxy-16α-methylpregna-1,4-diene-3,20-dione 17-benzoate | 21-Chloro-9α-fluoro-11β,17α-dihydroxy-16α-methyl-5β-pregnane-3,20-dione 17-benzoate |

EXAMPLE 112

9α-Fluoro-11β,17α-dihydroxy-16α-methyl-5β-pregnane-3,20-dione 17-propionate (I)

Following the general procedure of Example 106 and making non-critical variations but starting with 21-chloro-9α-fluoro-11β,17α-dihydroxy-16α-methyl-5β-pregnane-3,20-dione 17-propionate (Example 107) the title compound is obtained.

EXAMPLE 113

9α-Fluoro-11β,17α,21-trihydroxy-16α-methyl-5β-pregnane-3,20-dione 17,21-dipropionate (I)

9α-Fluoro-11β,17α,21-trihydroxy-16α-methylpregna-1,4-diene-3,20-dione 17,21-dipropionate (IA, 2.66 g.) in acetone (100 ml.) is hydrogenated in the presence of p-TSA hydrate (0.1 g.) and palladium on carbon (5%, 0.1 g.) until the uptake of hydrogen is complete. The mixture is filtered and the filtrate concentrated under reduced pressure. The crude product is column chromatographed on silica gel (100 g.) and eluted with acetone-methylene chloride (5/95). The appropriate fractions are pooled and concentrated to a solid. Crystallization of the solid from acetone-hexane gives the title compound, m.p. 176°; CMR 27.01δ; IR 3540, 1750, 1730, 1710, 1275, 1220, 1185, 1170, 1090, 1055, 1040, 1025, 1005 and 990 cm$^{-1}$.

EXAMPLE 114

9α-Fluoro-11β,17α,21-trihydroxy-5β-pregnane-3,20-dione 17,21-dipropionate (I)

9α-Fluoro-11β,17α,21-trihydroxypregna-1,4-diene-3,20-dione 17,21-dipropionate in acetone (100 ml.) containing triethylamine (2 ml.) is hydrogenated in the presence of palladium on carbon (5%, 0.1 g.) until the uptake of hydrogen is complete. The mixture is filtered and the filtrate is concentrated under reduced pressure. The residue is column chromatographed on silica gel (125 g.) packed in acetone-methylene choride (5:95) and eluted with the same mixture. The appropriate fractions (TLC) are pooled and concentrated to a solid which is crystallized from acetone-pentane. The crystalline product is pulverized and dried at 80° under high vacuum to afford the title compound, m.p. 153.2°–154°; [α]$_D$+4°; CMR 27.0δ; IR 3540, 1750, 1735, 1705, 1285, 1230, 1205, 1185, 1160, 1095, 1075, 1010 and 905 cm$^{-1}$.

EXAMPLE 115

9α-Chloro-11β,17α,21-trihydroxy-16β-methyl5β-pregnane-3,20-dione 17,21-dipropionate (I)

A mixture of beclomethasone dipropionate (9α-chloro-11β,17α,21-trihydroxy-16β-methylpregna-1,4-diene-3,20-dione 17,21-dipropionate, 3.0 g.) in ethyl acetate (200 ml.) is hydrogenated in the presence of palladium on carbon (5%, 0.3 g.) and pTSA (0.1 g.) for 2.5 hours and is then filtered. The filtrate is washed with cold aqueous potassium bicarbonate and saline and dried and evaporated under reduced pressure. The residue is column chromatographed on silica gel (300 g.) packed in acetone-methylene chloride (5/95). Elution is performed with the same solvent mixture. Appropriate fractions are pooled and concentrated to give the title compound.

EXAMPLE 116

9α,21-Dichloro-11β,17α-dihydroxy-16β-methyl-5β-pregnane-3,20-dione 17-propionate (I)

A mixture of 9α,21-dichloro-11β,17α-dihydroxy-16β-methylpregna-1,4-diene-3,20-dione 17-propionate (U.S. Pat. No. 3,721,687, 1.5 g.) in acetone (100 ml.) is hydrogenated in the presence of palladium on carbon (5%, 0.2 g.) for about 1 hour. The crude product is column chromatographed on silica gel (150 g.) packed in acetone-methylene chloride (5/95). Elution with acetone-methylene chloride mixture and crystallization of appropriate fractions from acetone-pentane gives the title compounds m.p. 148.5–149°; [α]$_D$+55°.

EXAMPLE 117

9α-Chloro-21-fluoro-11β,17α-dihydroxy-5β-pregnane-3,20-dione 17-propionate (I)

Following the general procedure of Example 116 and making non-critical variations but starting with 9α-chloro-21-fluoro-11β,17α-dihydroxypregna-1,4-diene-3,20-dione 17-propionate (German Offen 2,742,982), the title compound is obtained.

EXAMPLES 118 and 119

Following the general procedure of Example 116 and making non-critical variations but starting with the Δ$^4$-steriods of Column MM, the 5β-steriods of Column NN are obtained.

| Example | Column MM | Column NN |
|---|---|---|
| 118 | 9α,21-Dichloro-11β,17α-dihydroxypregn-4-ene-3,20-dione 17-propionate | 9α,21-Dichloro-11β,17α-dihydroxy-5β-pregnane-3,20-dione 17-propionate |
| 119 | 9α-Chloro-21-fluoro-11β,17α-dihydroxypregna-4-ene-3,20-dione 17-propionate | 9α-Chloro-21-fluoro-11β,17α-dihydroxy-5β-pregnane-3,20-dione 17-propionate |

EXAMPLE 120

11β,17α,21-Trihydroxy-16α-methyl-5β-pregnane-3,20-dione 17,21-dipropionate (I)

A mixture of 11β,17α,21-trihydroxy-16α-methylpregna-1,4-diene-3,20-dione 17,21-dipropionate (IA, 2.0 g.) in acetone (200 ml.) and triethylamine (2 ml.) is hydrogenated in the presence of palladium on carbon (5%, 0.1 g.) until the uptake of hydrogen is complete. The mixture is filtered and the filtrate concentrated under reduced pressure to a foam which is chromatographed on silica gel (150 g.), packed in acetone-methylene chloride (5/95). Elution is performed with the same acetone-methylene chloride mixture. The appropriate fractions are pooled and concentrated to give the title compound which is crystallized from diethylether-pentane, m.p. 142°–142.9°; NMR (CDCl$_3$) 4.82, 4.4, 1.25, 1.16, 1.06, and 0.95δ.

EXAMPLE 121

11β,17α,21-Trihydroxy-16β-methyl-5β-pregnane-3,20-dione 17,21-dipropionate (I)

Following the general procedure of Example 120 and making noncritical variations but starting with 11β,17α,21-trihydroxy-16β-methylpregna-1,4-diene-3,20-dione 17,21-dipropionate, the title compound is obtained.

EXAMPLE 122

7α-Chloro-11β,17α,21-trihydroxy-16α-methyl-5β-pregnane-3,20-dione 17,21-dipropionate Following the general procedure of Example 53 and making non-critical variations but starting with 7α-chloro-11β,17α,21-trihydroxy-16α-methylpregna-1,4-diene-3,20-dione 17,21-dipropionate (U.S. Pat. No. 4,124,707) the title compound is obtained.

EXAMPLE 123

21-Chloro-11β,17α-dihydroxy-5β-pregnane-3,20-dione 17-propionate (I)

Following the general procedure of Example 53 and making non-critical variations but starting with 21-chloro-11β,17α-dihydroxypregn-4-ene-3,20-dione (Japan, Kokai No. 77 83,446), the title compound is obtained.

EXAMPLE 124

21-Chloro-11β,17α-dihydroxy-5β-pregnane-3,20-dione 17-butyrate (I)

Following the general procedure of Example 53 and making non-critical variations but starting with 21-chloro-11β,17α-dihydroxypregna-4-ene-3,20-dione 17-butyrate (Japan, Kokai No. 77 83,446), the title compound is obtained.

EXAMPLE 125

21-Chloro-9,11-epoxy-17α-hydroxy-5β-pregnane-3,20-dione 17-propionate (II)

Following the general procedure of Example 53 and making non-critical variations but starting with 21-chloro-9,11-epoxy-17α-hydroxypregn-4-ene-3,20-dione 17-propionate, the title compound is obtained.

EXAMPLES 126-128

Following the general procedure of Example 125 and making non-critical variations but starting with the Δ4-steriods of Column OO, the 5β-steriods of Column PP are obtained.

| Example | Column OO | Column PP |
|---|---|---|
| 126 | 21-Chloro-9,11-epoxy-17α-hydroxy-16β-methyl-pregn-4-ene-3,20-dione 17-propionate | 21-Chloro-9,11-epoxy-17α-hydroxy-16β-methyl-5β-pregnane-3,20-dione 17-propionate |
| 127 | 21-Chloro-9,11-epoxy-17α-hydroxy-16α-methyl-pregn-4-ene-3,20-dione 17-propionate | 21-Chloro-9,11-epoxy-17α-hydroxy-16α-methyl-5β-pregnane-3,20-dione 17-propionate |
| 128 | 9,11-Epoxy-17α,21-dihydroxy-16β-methylpregn-4-ene-3,20-dione 17,21-dipropionate | 9,11-Epoxy-17α,21-dihydroxy-16β-methyl-5β-pregnane-3,20-dione 17,21-dipropionate |

EXAMPLE 129

9α,21-Dichloro-11β,17α-dihydroxy-5β-pregnane-3,20-dione 17-propionate (I)

To a solution of 21-chloro-9,11-epoxy-17α-hydroxy-5β-pregnane-3,20-dione 17-propionate (Example 125, 4.9 g.) in alcohol-free chloroform (250 ml.) containing tetrabutylammonium chloride (10 g. containing 15% n-butyl alcohol) is added slowly a chloroform solution of acetyl chloride (1.1 equivalents). The mixture is allowed to stand for 1 hr. at 20°-25° and is then concentrated under reduced pressure. The residue is column chromatographed on silica gel (500 g.) packed in acetone-methylene chloride. Elution with an acetone-methylene chloride mixture and pooling of the appropriate fractions gives the title compound.

EXAMPLE 130

9α-Fluoro-11β,17α,21-trihydroxy-16β-methyl-5β-pregnane-3,20-dione 17-valerate 21-dihydrogen phosphate (I)

A solution of 9α-fluoro-11β,17α,21-trihydroxy-16β-methyl-5β-pregnane 3,20-dione 17-valerate (Example 89, 1 g.) in THF (50 ml.) is added to a stirred solution of pyrophosphoryl chloride (0.65 ml.) in THF (10 ml.) at −50°. The temperature is allowed to rise slowly to −10° where it is held for five hours and then is allowed to stand at −4° for 18 hours. The mixture is diluted with water and concentrated under reduced pressure. The precipitate is collected and dissolved in ethyl acetate. The solution is washed with saline, dried and concentrated to give the title compound.

EXAMPLE 131

9α-Fluoro-11β,17α,21-trihydroxy-16β-methyl-5β-pregnane-3,20-dione 17-benzoate 21-dihydrogen phosphate (I)

Phosphorus oxychloride (8 g.) is added to a solution of 9α-fluoro-11β,17α,21-trihydroxy-16β-methyl-5β-pregnane-3,20-dione 17-benzoate (Example 93, 4 g.) in THF. The solution is cooled to −10°, pyridine (0.65 ml.) is added slowly, and the mixture is allowed to warm slowly to 20°-25° and stand for about 6 hours. The mixture is then diluted with ice water and concentrated under reduced pressure. The precipitate is collected, washed with water and suspended in aqueous methanol and sodium hydroxide (0.1 N) is added until the pH is 9.0. The aqueous solution is extracted with ethyl acetate, then acidified with dilute hydrochloric acid. The precipitate is collected, washed with water and dissolved in ethyl acetate. The ethyl acetate solution is washed with saline, dried and concentrated to give the title compound.

EXAMPLES 132-144

Following the general procedure of Examples 130 and 131, and making non-critical variations but starting with the 21-hydroxy steroids of Examples 90-103 (Column QQ), the 21-dihydrogen phosphate esters of Column RR are obtained.

| Example | Column QQ | Column RR |
|---|---|---|
| 132 | 90 | 9α-Fluoro-11β,17α,21-trihydroxy-16β-methyl-5β-pregnane-3,20-dione 17-acetate 21-dihydro- |

| Example | Column QQ | Column RR |
|---|---|---|
| 133 | 91 | 9α-Fluoro-11,17α,21-trihydroxy-16β-methyl-5-pregnane-3,20-dione 17-propionate 21-dihydrogen phosphate |
| 134 | 92 | 9α-Fluoro-11β,17α,21-trihydroxy-16β-methyl-5β-pregnane-3,20-dione 17-butyrate 21-dihydrogen phosphate |
| 135 | 94 | 9α-Fluoro-11β,17α,21-trihydroxy-16α-methyl-5β-pregnane-3,20-dione 17-acetate 21-dihydrogen phosphate |
| 136 | 95 | 9α-Fluoro-11β,17α,21-trihydroxy-16α-methyl-5β-pregnane-3,20-dione 17-propionate 21-dihydrogen phosphate |
| 137 | 96 | 9α-Fluoro-11β,17α,21-trihydroxy-16α-methyl-5β-pregnane-3,20-dione 17-butyrate 21-dihydrogen phosphate |
| 138 | 97 | 9α-Fluoro-11β,17α,21-trihydroxy-16α-methyl-5β-pregnane-3,20-dione 17-valerate 21-dihydrogen phosphate |
| 139 | 98 | 9α-Fluoro-11β,17α,21-trihydroxy-16α-methyl-5β-pregnane-3,20-dione 17-benzoate 21-dihydrogen phosphate |
| 140 | 99 | 9α-Fluoro-11β,17α,21-trihydroxy-5β-pregnane-3,20-dione 17-acetate 21-dihydrogen phosphate |
| 141 | 100 | 9α-Fluoro-11β,17α,21-trihydroxy-5β-pregnane-3,20-dione 17-propionate 21-dihydrogen phosphate |
| 142 | 101 | 9α-Fluoro-11β,17α,21-trihydroxy-5β-pregnane-3,20-dione 17-butyrate 21-dihydrogen phosphate |
| 143 | 102 | 9α-Fluoro-11β,17α,21-trihydroxy-5β-pregnane-3,20-dione 17-valerate 21-dihydrogen phosphate |
| 144 | 103 | 9α-Fluoro-11β,17α,21-trihydroxy-5β-pregnane-3,20-dione 17-benzoate 21-dihydrogen phosphate |

EXAMPLE 145

9α-Fluoro-11β,17α,21-trihydroxy-16β-methyl-5β-pregnane-3,20-dione 17-propionate 21-disodium phosphate (I)

A finely ground sample of 9α-fluoro-11β,17α,21-trihydroxy-16β-methyl-5β-pregnane-3,20-dione 17-propionate 21-dihydrogen phosphate (Example 133, 5 g.) is suspended in water (50 ml.) and stirred while sodium hydroxide (1 N) is added until the pH is 9. The solution is filtered and freeze dried to give the title compound.

EXAMPLES 146-159

Following the general procedure of Example 145, and making non-critical variations but starting with the 21-dihydrogen phosphate esters of Examples 130-144 (Column SS), there are obtained the corresponding 21-disodium phosphate ester salts of Column TT.

| Example | Column SS | Column TT |
|---|---|---|
| 146 | 132 | 9α-Fluoro-11β,17α,21-trihydroxy-16β-methyl-5β-pregnane-3,20-dione 17-acetate 21-disodium phosphate |
| 147 | 134 | 9α-Fluoro-11β,17α,21-trihydroxy-16β-methyl-5β-pregnane-3,20-dione 17-butyrate 21-disodium phosphate |
| 148 | 130 | 9α-Fluoro-11β,17α,21-trihydroxy-16β-methyl-5β-pregnane-3,20-dione 17-valerate 21-disodium phosphate |
| 149 | 131 | 9α-Fluoro-11β,17α,21-trihydroxy-16β-methyl-5β-pregnane-3,20-dione 17-benzoate 21-disodium phosphate |
| 150 | 135 | 9α-Fluoro-11β,17α,21-trihydroxy-16α-methyl-5β-pregnane-3,20-dione 17-acetate 21-disodium phosphate |
| 151 | 136 | 9α-Fluoro-11β,17α,21-trihydroxy-16α-methyl-5β-pregnane-3,20-dione 17-propionate 21-disodium phosphate |
| 152 | 137 | 9α-Fluoro-11β,17α,21-trihydroxy-16α-methyl-5β-pregnane-3,20-dione 17-butyrate 21-disodium phosphate |
| 153 | 138 | 9α-Fluoro-11β,17α,21-trihydroxy-16α-methyl-5β-pregnane-3,20-dione 17-valerate 21-disodium phosphate |
| 154 | 139 | 9α-Fluoro-11β,17α,21-trihydroxy-16α-methyl-5β-pregnane-3,20-dione 17-benzoate 21-disodium phosphate |
| 155 | 140 | 9α-Fluoro-11β,17α,21-trihydroxy-5β-pregnane-3,20-dione 17-acetate 21-disodium phosphate |
| 156 | 141 | 9α-Fluoro-11β,17α,21-trihydroxy-5β-pregnane-3,20-dione 17-propionate 21-disodium phosphate |
| 157 | 142 | 9α-Fluoro-11β,17α,21-trihydroxy-5β-pregnane-3,20-dione 17-butyrate 21-disodium phosphate |
| 158 | 143 | 9α-Fluoro-11β,17α,21-trihydroxy-5β-pregnane,3,20-dione 17-valerate 21-disodium phosphate |
| 159 | 144 | 9α-Fluoro-11β,17α,21-trihydroxy-5β-pregnane-3,20-dione-17-benzoate 21-disodium phosphate |

EXAMPLE 160

9α-Fluoro-11β,17α,21-trihydroxy-16β-methyl-5β-pregnane-3,20-dione 17-propionate 21-hemisuccinate (I)

A mixture of 9α-fluoro-11β,11α,21-trihydroxy-16β-methyl-5β-pregnane-3,20-dione 17-propionate (Example 91, 5.4 g.) and succinic anhydride (5.6 g.) in pyridine (46 ml.) is stirred overnight at 20°-25°. The reaction mixture is then poured slowly into a stirred mixture of ice water (1 l.) containing hydrochloric acid (46 ml.). The precipitate is collected, washed thoroughly with water and dried to give the title compound.

EXAMPLES 161-174

Following the general procedure of Example 160, and making non-critical variations but starting with the 21-hydroxy steroids of Examples 89-103 (Column UU), the 21-hemisuccinate esters of Column VV are obtained.

| Example | Column UU | Column VV |
|---|---|---|
| 161 | 90 | 9α-Fluoro-11β,17α,21-trihydroxy-16β-methyl-5β-pregnane-3,20-dione 17-acetate 21-hemisuccinate |
| 162 | 92 | 9α-Fluoro-11β,17α,21-trihydroxy-16β-methyl-5β-pregnane-3,20-dione 17-butyrate 21-hemisuccinate |
| 163 | 89 | 9α-Fluoro-11β,17α,21-trihydroxy-16β-methyl-5β-pregnane-3,20-dione 17-valerate 21-hemisuccinate |
| 164 | 93 | 9α-Fluoro-11β,17α,21-trihydroxy-16β-methyl-5β-pregnane-3,20-dione 17-benzoate 21-hemisuccinate |
| 165 | 94 | 9α-Fluoro-11β,17α,21-trihydroxy-16α-methyl-5β-pregnane-3,20-dione 17-acetate 21-hemisuccinate |
| 166 | 95 | 9α-Fluoro-11β,17α,21-trihydroxy-16α-methyl-5β-pregnane-3,20-dione 17-propionate 21-hemisuccinate |
| 167 | 96 | 9α-Fluoro-11β,17α,21-trihydroxy-16α-methyl-5β-pregnane-3,20-dione 17-butyrate 21-hemisuccinate |
| 168 | 97 | 9α-Fluoro-11β,17α,21-trihydroxy-16α-methyl-5β-pregnane-3,20-dione 17-valerate 21-hemisuccinate |
| 169 | 98 | 9α-Fluoro-11β,17α,21-trihydroxy-16α-methyl-5β-pregnane-3,20-dione 17-benzoate 21-hemisuccin- |

-continued

| Example | Column UU | Column VV |
|---|---|---|
| | | ate |
| 170 | 99 | 9α-Fluoro-11β,17α,21-trihydroxy-5β-pregnane-3,20-dione 17-acetate 21-hemisuccinate |
| 171 | 100 | 9α-Fluoro-11β,17α,21-trihydroxy-5β-pregnane-3,20-dione 17-propionate 21-hemisuccinate |
| 172 | 101 | 9α-Fluoro-11β,17α,21-trihydroxy-5β-pregnane-3,20-dione 17-butyrate 21-hemisuccinate |
| 173 | 102 | 9α-Fluoro-11β,17α,21-trihydroxy-5β-pregnane-3,20-dione 17-valerate 21-hemisuccinate |
| 174 | 103 | 9α-Fluoro-11β,17α,21-trihydroxy-5β-pregnane-3,20-dione 17-benzoate 21-hemisuccinate |

EXAMPLE 175

9α-Fluoro-11β,17α,21-trihydroxy-16β-methyl-5β-pregnane-3,20-dione 17-propionate 21-disodiumhemisuccinate (I)

A solution of 9α-fluoro-11β,17α,21-trihydroxy-16β-methyl-5β-pregnane-3,20-dione 17-propionate 21-hemisuccinate (Example 160, 1.53 g.) in acetone (10 ml.) is diluted with water (10 ml.) and a solution of sodium bicarbonate (0.248 g., 1.0 equivalent) in water (13.5 ml.) is added. The mixture is concentrated under reduced pressure and freeze-dried to give the title compound.

EXAMPLES 176–189

Following the general procedure of Example 175 and making non-critical variations but starting with the 21-hemisuccinate esters of Examples 161–174 (Column WW), the 21-sodium hemisuccinate ester salts of Column XX are obtained.

| Example | Column WW | Column XX |
|---|---|---|
| 176 | 161 | 9α-Fluoro-11β,17α,21-trihydroxy-16β-methyl-5β-pregnane-3,20-dione 17-acetate 21-sodium hemisuccinate |
| 177 | 162 | 9α-Fluoro-11β,17α,21-trihydroxy-16β-methyl-5β-pregnane-3,20-dione 17-butyrate 21-sodium hemisuccinate |
| 178 | 163 | 9α-Fluoro-11β,17α,21-trihydroxy-16β-methyl-5β-pregnane-3,20-dione 17-valerate 21-sodium hemisuccinate |
| 179 | 164 | 9α-Fluoro-11β,17α,21-trihydroxy-16β-methyl-5β-pregnane-3,20-dione 17-benzoate 21-sodium hemisuccinate |
| 180 | 165 | 9α-Fluoro-11β,17α,21-trihydroxy-16α-methyl-5β-pregnane-3,20-dione 17-acetate 21-sodium hemisuccinate |
| 181 | 166 | 9α-Fluoro-11β,17α,21-trihydroxy-16α-methyl-5β-pregnane-3,20-dione 17-propionate 21-sodium hemisuccinate |
| 182 | 167 | 9α-Fluoro-11β,17α,21-trihydroxy-16α-methyl-5β-pregnane-3,20-dione 17-butyrate 21-sodium hemisuccinate |
| 183 | 168 | 9α-Fluoro-11β,17α,21-trihydroxy-16α-methyl-5β-pregnane-3,20-dione 17-valerate 21-sodium hemisuccinate |
| 184 | 169 | 9α-Fluoro-11β,17α,21-trihydroxy-16α-methyl-5β-pregnane-3,20-dione 17-benzoate 21-sodium hemisuccinate |
| 185 | 170 | 9α-Fluoro-11β,17α,21-trihydroxy-5β-pregnane-3,20-dione 17-acetate 21-sodium hemisuccinate |
| 186 | 171 | 9α-Fluoro-11β,17α,21-trihydroxy-5β-pregnane-3,20-dione 17-propionate 21-sodium hemisuccinate |
| 187 | 172 | 9α-Fluoro-11β,17α,21-trihydroxy-5β-pregnane-3,20-dione 17-butyrate 21-sodium hemisuccinate |
| 188 | 173 | 9α-Fluoro-11β,17α,21-trihydroxy-5β-pregnane-3,20-dione 17-valerate 21-sodium hemisuccinate |
| 189 | 174 | 9α-Fluoro-11β,17α,21-trihydroxy-5β-pregnane-3,20-dione 17-benzoate 21-sodium hemisuccinate |

EXAMPLE 190

17α,21-Dihydroxy-16β-methyl-5α-pregn-9(11)-ene-3,20-dione 17-propionate (IVE)

A mixture of 17α,21-dihydroxy-16β-methyl-5α-pregn-9(11)-ene-3,20-dione (Preparation 18, 2.2 g.) in THF (45 ml.) containing triethylorthopropionate (2.2 ml.) and p-TSA (0.14 g.) is stirred for 0.5 hrs., then sulfuric acid (2 N, 2.2 ml.) is added. The mixture is allowed to stand an additional half hour at 30°, then is cooled, made basic with potassium bicarbonate (1 N, 15 ml.), diluted with water and concentrated under reduced pressure. The precipitate is collected, dissolved in ethyl acetate, washed with saline, dried and concentrated to give the title compound.

EXAMPLES 191–204

Following the general procedure of Preparations 15–18 and Example 190, but starting with 17α,21-dihydroxy-16β-methylpregna-4,9(11)-diene-3,20-dione 21-acetate (U.S. Pat. No. 3,072,685), 17α,21-dihydroxy-16α-methylpregna-4,9(11)-diene-3,20-dione 21-acetate and 17α,21-dihydroxypregna-4,9,(11)diene-3,20-dione 21-acetate and using for the esterifying agents trimethylorthoacetate, triethylorthopropionate, triethylorthobutyrate, trimethylorthovalerate, and trimethylorthobenzoate, according to the procedure of Example 190 the 5α-steriods of Column YY are obtained.

| Example | Column YY |
|---|---|
| 191 | 17α,21-Dihydroxy-16β-methyl-5α-pregn-9(11)-ene-3,20-dione 17-acetate |
| 192 | 17α,21-Dihydroxy-16β-methyl-5α-pregn-9(11)-ene-3,20-dione 17-butyrate |
| 193 | 17α,21-Dihydroxy-16β-methyl-5α-pregn-9(11)-ene-3,20-dione 17-valerate |
| 194 | 17α,21-Dihydroxy-16β-methyl-5α-pregn-9(11)-ene-3,20-dione 17-benzoate |
| 195 | 17α,21-Dihydroxy-16α-methyl-5α-pregn-9(11)-ene-3,20-dione 17-acetate |
| 196 | 17α,21-Dihydroxy-16α-methyl-5α-pregn-9(11)-ene-3,20-dione 17-propionate |
| 197 | 17α,21-Dihydroxy-16α-methyl-5α-pregn-9(11)-ene-3,20-dione 17-butyrate |
| 198 | 17α,21-Dihydroxy-16α-methyl-5α-pregn-9(11)-ene-3,20-dione 17-valerate |
| 199 | 17α,21-Dihydroxy-16α-methyl-5α-pregn-9(11)-ene-3,20-dione 17-benzoate |
| 200 | 17α,21-Dihydroxy-5α-pregn-9(11)-ene-3,20-dione 17-acetate |
| 201 | 17α,21-Dihydroxy-5α-pregn-9(11)-ene-3,20-dione 17-propionate |
| 202 | 17α,21-Dihydroxy-5α-pregn-9(11)-ene-3,20-dione 17-butyrate |
| 203 | 17α,21-Dihydroxy-5α-pregn-9(11)-ene-3,20-dione 17-valerate |
| 204 | 17α,21-Dihydroxy-5α-pregn-9(11)-ene-3,20-dione 17-benzoate |

EXAMPLE 205

17α,21-Dihydroxy-16β-methyl-5α-pregn-9(11)-ene-3,20-dione 17-propionate 21-mesylate A mixture of 17α,21-Dihydroxy-16β-methyl-5α-pregn-9(11)-ene-3,20-dione 17-propionate (Example 190, 4.1 g.) in pyridine (20 ml.) is cooled to 0° and methanesulfonylchloride (5 ml.) is added slowly. After stirring for 1 hour at 0°, the reaction mixture is poured into a mixture of ice and water containing hydrochloric acid (15 ml.). The precipitate is collected, dissolved in methylene chloride and washed successively with aqueous potassium bisulfate, water and aqueous potassium bicarbonate. The extract is concentrated to a foam which is chromatographed on silica gel (500 g.) and eluted with acetone-methylene chloride mixtures. Appropriate fractions are pooled and concentrated to give the title compound.

EXAMPLE 206

21-Chloro-9α-fluoro-11β,17α-dihydroxy-16β-methyl-5α-pregnane-3,20-dione 17-propionate (IV)

Step 1: 9α-Bromo-11β,17α,21-trihydroxy-16β-methyl-5α-pregnane-3,20-dione 17-propionate 21-mesylate A mixture of 17α,21-Dihydroxy-16β-methyl-5α-pregn-9(11)-ene-3,20-dione 17-propionate 21-mesylate (Example 205, 12.9 g.) in t-butyl alcohol (5 ml.) and methylene chloride (40 ml.) is mixed with a solution of perchloric acid (70%, 36 ml.) in water (490 ml.) and then a solution of N-bromoacetamide (6.6 g.) in t-butyl alcohol (70 ml.) is added at 20°-25°. The mixture is stirred for 0.5 hours at 20°-25°, then is diluted with a solution of sodium sulfite (6.6 g.) in water (70 ml.), concentrated under reduced pressure to remove the methylene chloride, then further diluted with water (1 l.) and concentrated. The precipitate is collected and dried to give 9α-bromo-11β,17α,21-trihydroxy-16β-methyl-5α-pregnane-3,20-dione 17-propionate 21-mesylate.

Step 2: 9,11-Epoxy-17α,21-dihydroxy-16β-methyl-5α-pregnane-3,20-dione 17-propionate 21-mesylate A solution of 9α-bromo-11β,17α,21-trihydroxy-16β-methyl-5α-pregnane-3,20-dione 17-propionate 21-mesylate (Step 1, 2.9 g.) in THF (200 ml.) is cooled to 5° and 1,8-diazabicyclo[5.4.0]undec-7-ene (DBU, 1 ml.) is added. The mixture was allowed to warm to 20°-25° and stand for several hours at 20°-25°. The reaction mixture is then diluted with water (380 ml.) and concentrated under reduced pressure to give a precipitate which is dissolved in methylene chloride. The solution is washed with aqueous potassium bisulfate, water and aqueous potassium bicarbonate and dried and concentrated to give a solid which is chromatographed on silica gel. Elution is performed with acetonemethylene chloride mixtures and the appropriate fractions are pooled and concentrated under reduced pressure. The product is crystallized from acetone-ether to give 9,11-epoxy-17α,21-dihydroxy-16β-methyl-5α-pregnane-3,20-dione 17-propionate 21-mesylate, m.p. 140°-142°; NMR (CDCl$_3$) 0.89, 1.18, 1.20, 1.34, 3.17, 3.45 and 4.68δ.

Step 3: 21-Chloro-9,11-epoxy-17α-hydroxy-16β-methyl-5α-pregnane-3,20-dione 17-propionate A mixture of 9,11-epoxy-17α,21-dihydroxy-16β-methyl-5α-pregnane-3,20-dione 17-propionate 21-mesylate (Step 2, 4 g.) and lithium chloride (8 g.) in DMF (100 ml.) and acetone (100 ml.) is heated under reflux for about 100 hours. The reaction mixture is concentrated under reduced pressure and diluted with water. The precipitate is collected, dried and chromatographed on silica gel (200 g.). The column is eluted with acetone-methylene chloride; the appropriate fractions are pooled and concentrated to give 21-chloro-9,11-epoxy-17α-hydroxy-16β-methyl-5α-pregnane-3,20-dione 17-propionate.

Step 4: 21-Chloro-9α-fluoro-11β,17α-dihydroxy-16β-methyl-5α-pregnane-3,20-dione 17-propionate (IV)

Following the general procedure of (Example 290-298, Step 3) and making non-critical variations but starting with 21-chloro-9,11-epoxy-17α-hydroxy-16β-methyl-5α-pregnane-3,20-dione 17-propionate (Step 3), the title compound is obtained, m.p. 195°; NMR (CDCl$_3$) 0.95, 1.18, 1.35, 4.0, 4.25δ; IR (mull) 3500, 1720, 1295, 1245, 1020, 1005, 995 and 895 cm$^{-1}$.

EXAMPLES 207-220

Following the general procedure of Example 205 and 206 and making non-critical variations but starting with the Δ$^{9,(11)}$-21-hydroxy-steroids of Example 191-204 (Column ZZ) the 21-chloro steroids of Column AAA are obtained.

| Example | Column ZZ | Column AAA |
|---|---|---|
| 207 | 191 | 21-Chloro-9α-fluoro-11β,17α-dihydroxy-16β-methyl-5α-pregnane-3,20-dione 17-acetate |
| 208 | 192 | 21-Chloro-9α-fluoro-11β,17α-dihydroxy-16β-methyl-5α-pregnane-3,20-dione 17-butyrate |
| 209 | 193 | 21-Chloro-9α-fluoro-11β,17α-dihydroxy-16β-methyl-5α-pregnane-3,20-dione 17-valerate |
| 210 | 194 | 21-Chloro-9α-fluoro-11β,17α-dihydroxy-16β-methyl-5α-pregnane-3,20-dione 17-benzoate |
| 211 | 195 | 21-Chloro-9α-fluoro-11β,17α-dihydroxy-16α-methyl-5α-pregnane-3,20-dione 17-acetate |
| 212 | 196 | 21-Chloro-9α-fluoro-11β,17α-dihydroxy-16α-methyl-5α-pregnane-3,20-dione 17-propionate |
| 213 | 197 | 21-Chloro-9α-fluoro-11β,17α-dihydroxy-16α-methyl-5α-pregnane-3,20-dione 17-butyrate |
| 214 | 198 | 21-Chloro-9α-fluoro-11β,17α-dihydroxy-16α-methyl-5α-pregnane-3,20-dione 17-valerate |
| 215 | 199 | 21-Chloro-9α-fluoro-11β,17α-dihydroxy-16α-methyl-5α-pregnane-3,20-dione 17-benzoate |
| 216 | 200 | 21-Chloro-9α-fluoro-11β,17α-dihydroxy-5α-pregnane-3,20-dione 17-acetate |
| 217 | 201 | 21-Chloro-9α-fluoro-11β,17α-dihydroxy-5α-pregnane-3,20-dione 17-propionate |
| 218 | 202 | 21-Chloro-9α-fluoro-11β,17α-dihydroxy-5α-pregnane-3,20-dione 17-butyrate |
| 219 | 203 | 21-Chloro-9α-fluoro-11β,17α-dihydroxy-5α-pregnane-3,20-dione 17-valerate |
| 220 | 204 | 21-Chloro-9α-fluoro-11β,17α-dihydroxy-5α-pregnane-3,20-dione 17-benzoate |

EXAMPLE 221

9α-Fluoro-11β,17α-dihydroxy-16β-methyl-5α-pregnane-3,20-dione 17-propionate (IV)

A sample of 21-chloro-9α-fluoro-11β,17α-dihydroxy-16β-methyl-5α-pregnane-3,20-dione 17-propionate (Example 206, 8 g.) in acetone (200 ml.) containing triethylamine (4 ml.) is hydrogenated at 2 atmospheres in the presence of palladium on carbon (5%, 0.8 g.) until the uptake of hydrogen is complete. The mixture is filtered and the filtrate is concentrated under reduced pressure. The residue is chromatographed on silica gel (400 g.) and eluted with acetone-methylene chloride mixtures. The appropriate fractions are pooled and concentrated under reduced pressure to give the title compound.

EXAMPLES 222–235

Following the general procedure of Example 221 and making non-critical variations but starting with the 17-acetate, 17-butyrate, 17-valerate or 17-benzoate esters of 21-chloro-9α-fluoro-11β,17α-dihydroxy-16β-methyl-5α-pregnane-3,20-dione (Examples 207–210), there are obtained the corresponding 21-unsubstituted esters, namely the 17-acetate, 17-butyrate, 17-valerate, or 17-benzoate esters of 9α-fluoro-11β,17α-dihydroxy-16β-methyl-5α-pregnane-3,20-dione are obtained.

Following the procedure of Example 221 and making non-critical variations but starting with the 17-acetate, 17-propionate, 17-butyrate, 17-valerate or 17-benzoate esters of 21-chloro-9α-fluoro-11β,17α-dihydroxy-16α-methyl-5α-pregnane-3,20-dione and 21-chloro-9α-fluoro-11β,17α-dihydroxy-5α-pregnane-3,20-dione (Examples 211–220), the corresponding 21-unsubstituted esters, namely the 17-acetate, 17-propionate, 17-butyrate, 17-valerate or 17-benzoate esters of 9α-fluoro-11β,17α-dihydroxy-16α-methyl-5α-pregnane-3,20-dione and 9α-fluoro-11β,17α-dihydroxy-5α-pregnane-3,20-dione are obtained.

EXAMPLE 236

21-Chloro-9α-fluoro-17α-hydroxy-16β-methyl-5α-pregnane-3,11,20-trione 17-propionate (IV)

Jones reagent (chromium trioxide-aqueous sulfuric acid, 2.6 ml.) is added to a solution of 21-chloro-9α-fluoro-11β,17α-dihydroxy-16β-methyl-5α-pregnane-3,20-dione 17-propionate (Example 206, 4 g.) in acetone (100 ml.). The mixture is stirred for one-half hour at 20°–25°. Isopropyl alcohol is added followed by slow addition of ice water (600 ml.). The mixture is concentrated under reduced pressure and filtered. The crude product is dried and chromatographed on silica gel (400 g.), eluting with an acetone-methylene chloride mixture. The appropriate fractions are pooled and concentrated under reduced pressure to give the title compound.

EXAMPLES 237–250

Following the procedure of Example 236 and making non-critical variations but starting with the 17-acetate, 17-butyrate, 17-valerate or 17-benzoate esters (Examples 207–210) of 21-chloro-9α-fluoro-11β,17α-dihydroxy-16β-methyl-5α-pregnane-3,20-dione the corresponding trione esters, namely the 17-acetate, 17-butyrate, 17-valerate and 17-benzoate esters, of 21-chloro-9α-fluoro-17α-hydroxy-16β-methyl-5α-pregnane-3,11,20-trione are obtained.

Following the general procedure of Example 236 and making non-critical variations but starting with the 17-acetate, 17-propionate, 17-butyrate, 17-valerate or 17-benzoate esters of 21-chloro-9α-fluoro-11β,17α-dihydroxy-16α-methyl-5α-pregnane-3,20-dione and 21-chloro-9α-fluoro-11β,17α-dihydroxy-5α-pregnane-3,20-dione (Examples 211–220), the corresponding trione esters, namely the 17-acetate, 17-propionate, 17-butyrate, 17-valerate or 17-benzoate esters of 21-chloro-9α-fluoro-17α-hydroxy-16α-methyl-5α-pregnane-3,11,20-trione and 21-chloro-9α-fluoro-17α-hydroxy-5α-pregnane-3,11,20-trione are obtained.

EXAMPLE 251

9α,11β,21-Trichloro-17α-hydroxy-16β-methyl-5α-pregnane-3,20-dione 17-propionate (IV)

Step 1: 21-Chloro-17α-hydroxy-16β-methyl-5α-pregn-9(11)-ene-3,20-dione 17-propionate Following the general procedure of Example 206, Step 3, and making non-critical variations but starting with 17α,21-dihydroxy-16β-methyl-5α-pregn-9(11)-ene-3,20-dione 17-propionate 21-mesylate, (Example 205) 21-chloro-17α-hydroxy-16β-methyl-5α-pregn-9(11)-ene-3,20-dione 17-propionate is obtained.

Step 2: 9α,11β,21-Trichloro-17α-hydroxy-16β-methyl-5α-pregnane-3,20-dione 17-propionate A mixture of 21-chloro-17α-hydroxy-16β-methyl-5α-pregn-9(11)-ene-3,20-dione 17-propionate (Step 1, 1.3 g.) in chloroform (100 ml.) and pyridine (1 ml.) is cooled to −10°. The chlorine solution in carbon tetrachloride (40 ml., 1.15 equivalents) is added at −10° and the reaction mixture is washed successively with cold aqueous potassium bisulfate, water and cold aqueous potassium bicarbonate. The organic extract is dried and concentrated and the residue is chromatographed on silica gel. The column is eluted with an acetone-methylene chloride mixture. The appropriate fractions are pooled and concentrated under reduced pressure to give the title compound.

EXAMPLES 252–265

Following the general procedure of Examples 205 and 251, and making non-critical variations but starting with the 17-acetate, 17-butyrate, 17-valerate and 17-benzoate esters of 17α,21-dihydroxy-16β-methylpregn-9(11)-ene-3,20-dione (Examples 191–194), the corresponding trichlorinated steroids, namely the 17-acetate, 17-butyrate, 17-valerate and 17-benzoate of 9α,11β,21-trichloro-17α-hydroxy-16β-methyl-5α-pregnane-3,20-dione are obtained.

Following the general procedure of Examples 205 and 251 and making non-critical variations but starting with the 17-acetate, 17-propionate, 17-butyrate, 17-valerate and 17-benzoate esters of 17α,21-dihydroxy-16α-methyl-5α-pregn-9(11)-ene-3,20-dione and 17α,21-dihydroxy-5α-pregn-9(11)-ene-3,20-dione (Examples 195–204) the corresponding trichlorinated steroids, namely the 17-acetate, 17-propionate, 17-butyrate, 17-valerate and 17-benzoate esters of 9α,11β,21-trichloro-17α-hydroxy-16α-methyl-5α-pregna-3,20-dione and 9α,11β,21-trichloro-17α-hydroxy-5α-pregna-3,20-dione are obtained.

EXAMPLES 266–280

Following the general procedure of Example 383 and making non-critical variations but starting with the 17-acetate 21-mesylate, 17-propionate, 21-mesylate, 17-butyrate 21-mesylate, 17-valerate 21-mesylate or 17-benzoate 21-mesylate diesters of 9α-bromo-11β,17α,21-trihydroxy-16β-methyl-5α-pregnane-3,20-dione, 9α-bromo-11β,17α,21-trihydroxy-16α-methyl-5α-pregnane-3,20-dione and 9α-bromo-11β,17α,21-trihydroxy-5α-pregnane-3,20-dione, (Examples 206–220, Step 1) the corresponding 9-unsubstituted diesters, namely the 17-acetate 21-mesylate, 17-propionate 21-mesylate, 17-butyrate 21-mesylate, 17-valerate 21-mesylate or 17-benzoate 21-mesylate diesters of 11β,17α,21-trihydroxy-16β-methyl-5α-pregnane-3,20-dione, 11β,17α,21-trihydroxy-16α-methyl-5α-pregnane-3,20-dione and 11β,17α,21-trihydroxy-5α-pregnane-3,20-dione are obtained.

EXAMPLE 281

17α,21-Dihydroxy-16β-methyl-5α-pregn-9(11)ene-3,20-dione 17,21-dipropionate

A solution of 17α,21-dihydroxy-16β-methyl-5α-pregn-9(11)-ene-3,20-dione 17-propionate (Example 190, 2 g.) in pyridine (8 ml.) and propionic anhydride (4 ml.) was allowed to stand overnight at 20°-25°. The mixture is then diluted with ice and water to give a precipitate which was collected and dried. The crude produce is chromatographed on silica gel (200 g.) and eluted with acetone-methylene chloride mixtures. The appropriate fractions are pooled and concentrated to give the title compound.

EXAMPLE 282

Following the general procedure of Example 281 and making non-critical variations but using acetic anhydride in place of propionic anhydride the corresponding 21-ester, namely 17α,21-dihydroxy-16β-methyl-5α-pregn-9(11)-ene-3,20-dione 17-propionate 21-acetate is obtained.

EXAMPLES 283 AND 284

Following the general procedure of Examples 281 and 282 and making non-critical variations but starting with 17α,21-dihydroxy-16α-methyl-5α-pregn-9(11)-ene-3,20-dione 17-propionate (Example 196), the corresponding 17,21-diesters, namely 17α,21-dihydroxy-16α-methyl-5α-pregn-9(11)-ene-3,20-dione 17-propionate 21-acetate and 17α,21-dihydroxy-16α-methyl-5α-pregn-9(11)-ene-3,20-dione 17,21-dipropionate are obtained.

EXAMPLE 285 AND 286

Following the general procedure of Examples 281 and 282 and making non-critical variations but starting with 17α,21-dihydroxy-5α-pregn-9(11)-ene-3,20-dione 17-propionate (Example 201), the corresponding 21-esters, namely the 17α,21-dihydroxy-5α-pregn-9(11)-ene-3,20-dione 17-propionate 21-acetate and 17α,21-dihydroxy-5α-pregn-9(11)-ene-3,20-dione 17,21-dipropionate are obtained.

EXAMPLES 287–289

Following the general procedure of Example 282 and making non-critical variations but starting with the 17-butyrate esters of 17α,21-dihydroxy-16β-methyl-5α-pregn-9(11)-ene-3,20-dione, 17α,21-dihydroxy-16α-methyl-5α-pregn-9(11)-ene-3,20-dione or 17α,21-dihydroxy-5α-pregn-9(11)-ene-3,20-dione (Examples 192, 197 and 202) the corresponding 17,21-diesters, namely the 17-butyrate 21-acetate diesters of 17α,21-dihydroxy-16β-methyl-5α-pregn-9(11)-ene-3,20-dione, 17α,21-dihydroxy-6α-methyl-5α-pregn-9(11)-ene-3,20-dione, or 17α,21-dihydroxy-5α-pregn-9(11)-ene-3,20-dione are obtained.

EXAMPLES 290–298

Step 1
Following the general procedure of Example 206, Step 1, and making non-critical variations but starting with the 17-propionate 21-acetate, 17,21-dipropionate, or 17-butyrate 21-acetate diesters of 17α,21-dihydroxy-16β-methyl-5α-pregn-9(11)-ene-3,20-dione, 17α,21-dihydroxy-16α-methyl-5α-pregn-9(11)-ene-3,20-dione and 17α,21-dihydroxy-5α-pregn-9(11)-ene-3,20-dione (Examples 281–289) the corresponding bromohydrins, namely the 17-propionate 21-acetate, 17,21-dipropionate, or 17-butyrate 21-acetate diesters of 9α-bromo-11β,17α,21-trihydroxy-16β-methyl-5α-pregnane-3,20-dione, 9α-bromo-11β,17α,21-trihydroxy-16α-methyl-5α-pregnane-3,20-dione and 9α-bromo-11β,17α,21-trihydroxy-5α-pregnane-3,20-dione are obtained.

Step 2
Following the general procedure of Example 206, Step 2, and making non-critical variations but starting with the 17-propionate 21-acetate, 17,21-dipropionate, or 17-butyrate 21-acetate diesters of 9α-bromo-11β,17α,21-trihydroxy-16β-methyl-5α-pregnane-3,20-dione, 9α-bromo-11β,17α,21-trihydroxy-16α-methyl-5α-pregnane-3,20-dione and 9α-bromo-11β,17α,21-trihydroxy-5α-pregnane-3,20-dione (Step 1), the corresponding 9,11-epoxides, namely the 17-propionate 21-acetate, 17,21-dipropionate or 17-butyrate 21-acetate diesters of 9,11-epoxy-17α,21-dihydroxy-16β-methyl-5α-pregnane-3,20-dione, 9,11-epoxy-17α,21-dihydroxy-16α-methyl-5α-pregnane-3,20-dione and 9,11-epoxy-17α,21-dihydroxy-5α-pregnane-3,20-dione are obtained.

Step 3: 9α-Fluoro-11β,17α,21-trihydroxy-16β-methyl-5α-pregnane-3,20-dione 17,21-dipropionate (IV)

A sample of 9,11-epoxy-17α,21-dihydroxy-16β-methyl-5α-pregnane-3,20-dione 17,21-dipropionate (Step 2) is added to a stirred mixture of hydrogen fluoride (9.2 g.), methylene chloride (6.6 ml.) and water (3.57 ml.) at $-70°$. The mixture is stirred for one hour at $-70°$ and then one hour at $-30°$, then cooled to $-70°$ and diluted with cold THF (14 ml.). The reaction mixture is then poured into a cold stirred mixture of potassium carbonate, water and THF. The aqueous phase is separated, diluted with water and extracted with methylene chloride. The organic extracts are combined, washed with water, dried and concentrated under reduced pressure. The residue is chromatographed on silica gel (200 g.), eluted with an acetone-methylene chloride mixture. The appropriate fractions are pooled and concentrated under reduced pressure. Crystallization of the residue from hexane-ether gives the title compound, m.p. 147.5°–147.6°; NMR (CDCl$_3$) 0.94, 1.16, 1.18. 1.36. 4.28, 4.57; CMR 14.51 δ; IR (mull) 3360, 1750, 1735, 1700, 1360, 1345, 1070, 1020, 1185, 1175, 975, 940 and 880 cm$^{-1}$.

Following the general procedure of Step 3 above and making non-critical variations but starting with the 17-propionate 21-acetate or 17-butyrate 21-acetate diesters of 9,11-epoxy-17α,21-dihydroxy-16β-methyl-5α-pregnane-3,20-dione (Step 2), the corresponding fluorohydrins, namely the 17-propionate 21-acetate and 17-butyrate 21-acetate diesters of 9α-fluoro-11,17α,21-trihydroxy-16β-methyl-5α-pregnane-3,20-dione are obtained.

Following the procedure of Step 3 above and making non-critical variations but starting with the 17-propionate 21-acetate, 17,21-dipropionate or 17-butyrate 21-acetate diesters of 9,11-epoxy-17α,21-dihydroxy-16α-methyl-5α-pregnane-3,20-dione and 9,11-epoxy-17α,21-dihydroxy-5α-pregnane-3,20-dione (Step 2) the corresponding fluorohydrins, namely the 17-propionate 21-acetate, 17,21-dipropionate, or 17-butyrate 21-acetate diesters of 9α-fluoro-11β,17α,21-trihydroxy-16α-methyl-5α-pregnane-3,20-dione and 9α-fluoro- 11β,17α,21-trihydroxy-5α-pregnane-3,20-dione are obtained.

EXAMPLE 299

9α-Fluoro-11β,17α,21-trihydroxy-16β-methyl-5α-pregnane-3,20-dione 17-propionate (IV)

Step 1: 9-Fluoro-11β,17α,21-trihydroxy-16β-methyl-5α-pregnane-3,20-dione

A mixture of 9α-fluoro-11β,17α,21-trihydroxy-16β-methyl-5α-pregnane-3,20-dione 17,21-dipropionate (Example 290, 2.1 g.) in methanol (70 ml.) and aqueous potassium carbonate (10%, 15 ml.) is stirred for about 1 hour under a nitrogen atmosphere. The mixture is then acidified with acetic acid, diluted with water and concentrated under reduced pressure. The mixture is cooled and the solid is collected, washed with water and dried to give 9α-fluoro-11β,17α,21-trihydroxy-16β-methyl-5α-pregnane-3,20-dione.

Step 2: 9α-Fluoro-11β,17α,21-trihydroxy-16β-methyl-5α-pregnane-3,20-dione 17-propionate A mixture of 9α-fluoro-11β,17α,21-trihydroxy-16β-methyl-5α-pregnane-3,20-dione (Step 1, 1.1 g.) in THF (25 ml.) containing triethylorthopropionate (1.2 ml.) and p-TSA (1.07 g.) is allowed to stand at 30° for about 1 hour and then sulfuric acid (2 N, 1.2 ml.) is added. The mixture is stirred for an additional half hour, then made basic with potassium carbonate (1 N, 7 ml.) diluted with water and concentrated under reduced pressure. The precipitate is collected, dissolved in ethyl acetate, washed with saline, dried and concentrated to give the title compound.

EXAMPLES 300–313

Step 1

Following the general procedure of Example 299, Step 1, and making non-critical variations but starting with the 17,21-dipropionate, 17-propionate 21-acetate, and 17-butyrate 21-acetate diesters of 9α-fluoro-11β,17α,21-trihydroxy-16β-methyl-5α-pregnane-3,20-dione, 9α-fluoro-11β,17α,21-trihydroxy-16α-methyl-5α-pregnane-3,20-dione and 9α-fluoro-11β,17α,21-trihydroxy-5α-pregnane-3,20-dione (Examples 290-298), the corresponding triols, namely 9α-fluoro-11β,17α,21-trihydroxy-16β-methyl-5α-pregnane-3,20-dione, 9α-fluoro-11β,17α,21-trihydroxy-5α-pregnane-3,20-dione and 9α-fluoro-11β,17α,21-trihydroxy-5α-pregnane-3,20-dione are obtained.

Step 2

Following the general procedure of Example 299, Step 2, and making non-critical variations but substituting trimethylorthoacetate, triethylorthobutyrate, trimethylorthovalerate, or trimethylorthobenzoate for trimethylorthopropionate, the corresponding 17-esters, namely the 17-acetate, 17-butyrate, 17-valerate and 17-benzoate esters of 9α-fluoro-11β,17α,21-trihydroxy-16β-methyl-5α-pregnane-3,20-dione are obtained.

Following the general procedure of Example 299, Step 2, and making non-critical variations but starting with 9α-fluoro-11β,17α,21-trihydroxy-16α-methyl-5α-pregnane-3,20-dione and 9α-fluoro-11β,17α,21-trihydroxy-5α-pregnane-3,20-dione, the corresponding 17α-esters, namely the 17-acetate, 17-propionate, 17-butyrate, 17-valerate or 17-benzoate esters of 9α-fluoro-11β,17α,21-trihydroxy-16α-methyl-5α-pregnane-3,20-dione and 9α-fluoro-11β,17α,21-trihydroxy-5α-pregnane-3,20-dione are obtained.

EXAMPLE 314

9α-Fluoro-11β,17α,21-trihydroxy-16β-methyl-5α-pregnane-3,20-dione 17-valerate 21-dihydrogen phosphate (IV)

A solution of 9α-fluoro-11β,17α,21-trihydroxy-16β-methyl-5β-pregnane 3,20-dione 17-valerate (Example 302, 1 g.) in THF (50 ml.) is added to a stirred solution of pyrophosphoryl chloride (0.65 ml.) in THF (10 ml.) at −50°. The temperature is allowed to rise slowly to −10° where it is held for five hours and then is allowed to stand at −4° for 18 hours. The mixture is diluted with water and concentrated under reduced pressure. The precipitate is collected and dissolved in ethyl acetate. The solution is washed with saline, dried and concentrated to give the title compound.

EXAMPLE 315

9α-Fluoro-11β,17α,21-trihydroxy-16β-methyl-5α-pregnane-3,20-dione 17-benzoate 21-dihydrogen phosphate (IV)

Phosphorus oxychloride (8 g.) is added to a solution of 9α-fluoro-11β,17α,21-trihydroxy-16β-methyl-5β-pregnane-3,20-dione 17-benzoate (Example 303, 4 g.) in THF. The solution is cooled to −10°, pyridine (0.65 ml.) is added slowly, and the mixture is allowed to warm slowly to 20°–25° and stand for about 6 hours. The mixture is then diluted with ice water and concentrated under reduced pressure. The precipitate is collected, washed with water and suspended in aqueous methanol and sodium hydroxide (0.1 N) is added until the pH is 9.0. The aqueous solution is extracted with ethyl acetate, then acidified with dilute hydrochloric acid. The precipitate is collected, washed with water and dissolved in ethyl acetate. The ethyl acetate solution is washed with saline, dried and concentrated to give the title compound.

EXAMPLES 316–328

Following the general procedure of Examples 314 and 315, and making non-critical variations but starting with the 21-hydroxy steroids of Examples 299–313 (Column BBB), the 21-dihydrogen phosphate esters of Column CCC are obtained.

| Example | Column BBB | Column CCC |
|---|---|---|
| 316 | 300 | 9α-Fluoro-11β,17α,21-trihydroxy-16β-methyl-5α-pregnane-3,20-dione 17-acetate 21-dihydrogen phosphate |
| 317 | 299 | 9α-Fluoro-11β,17α,21-trihydroxy-16β-methyl-5α-pregnane-3,20-dione 17-propionate 21-dihydrogen phosphate |
| 318 | 301 | 9α-Fluoro-11β,17α,21-trihydroxy-16β-methyl-5α-pregnane-3,20-dione 17-butyrate 21-dihydrogen phosphate |
| 319 | 304 | 9α-Fluoro-11β,17α,21-trihydroxy-16α-methyl-5α-pregnane-3,20-dione 17-acetate 21-dihydrogen phosphate |
| 320 | 305 | 9α-Fluoro-11β,17α,21-trihydroxy-16α-methyl-5α-pregnane-3,20-dione 17-propionate 21-dihydrogen phosphate |
| 321 | 306 | 9α-Fluoro-11β,17α,21-trihydroxy-16α-methyl-5α-pregnane-3,20-dione 17-butyrate 21-dihydrogen phosphate |
| 322 | 307 | 9α-Fluoro-11β,17α,21-trihydroxy-16α-methyl-5α-pregnane-3,20-dione 17-valerate 21-dihydrogen phosphate |
| 323 | 308 | 9α-Fluoro-11β,17α,21-trihydroxy-16α-methyl-5α-pregnane-3,20-dione 17-benzoate 21-dihydrogen |

-continued

| Example | Column BBB | Column CCC |
|---|---|---|
| 324 | 309 | 9α-Fluoro-11β,17α,21-trihydroxy-5α-pregnane-3,20-dione 17-acetate 21-dihydrogen phosphate |
| 325 | 310 | 9α-Fluoro-11β,17α,21-trihydroxy-5α-pregnane-3,20-dione 17-propionate 21-dihydrogen phosphate |
| 326 | 311 | 9α-Fluoro-11β,17α,21-trihydroxy-5α-pregnane-3,20-dione 17-butyrate 21-dihydrogen phosphate |
| 327 | 312 | 9α-Fluoro-11β,17α,21-trihydroxy-5α-pregnane-3,20-dione 17-valerate 21-dihydrogen phosphate |
| 328 | 313 | 9α-Fluoro-11β,17α,21-trihydroxy-5α-pregnane-3,20-dione 17-benzoate 21-dihydrogen phosphate |

EXAMPLE 329

9α-Fluoro-11β,17α,21-trihydroxy-16β-methyl-5α-pregnane-3,20-dione 17-propionate 21-disodium phosphate (IV)

A finely ground sample of 9α-fluoro-11β,17α,21-trihydroxy-16β-methy-5α-pregnane-3,20-dione 17-propionate 21-dihydrogen phosphate (Example 316, 5 g.) is suspended in water (50 ml.) and stirred while sodium hydroxide (1 N) is added until the pH is 9. The solution is filtered and freeze dried to give the title compound.

EXAMPLES 330–331

Following the general procedure of Example 329, and making non-critical variations but starting with the 21-dihydrogen phosphate esters of Examples 314–328 (Column DDD), there are obtained the corresponding 21-disodium phosphate ester salts of Column EEE.

| Example | Column DDD | Column EEE |
|---|---|---|
| 330 | 317 | 9α-Fluoro-11β,17α,21-trihydroxy-16β-methyl-5α-pregnane-3,20-dione 17-acetate 21-disodium phosphate |
| 331 | 318 | 9α-Fluoro-11β,17α,21-trihydroxy-16β-methyl-5α-pregnane-3,20-dione 17-butyrate 21-disodium phosphate |
| 332 | 314 | 9α-Fluoro-11β,17α,21-trihydroxy-16β-methyl-5α-pregnane-3,20-dione 17-valerate 21-disodium phosphate |
| 333 | 315 | 9α-Fluoro-11β,17α,21-trihydroxy-16β-methyl-5α-pregnane-3,20-dione 17-benzoate 21-disodium phosphate |
| 334 | 319 | 9α-Fluoro-11β,17α,21-trihydroxy-16α-methyl-5α-pregnane-3,20-dione 17-acetate 21-disodium phosphate |
| 335 | 320 | 9α-Fluoro-11β,17α,21-trihydroxy-16α-methyl-5α-pregnane-3,20-dione 17-propionate 21-disodium phosphate |
| 336 | 321 | 9α-Fluoro-11β,17α,21-trihydroxy-16α-methyl-5α-pregnane-3,20-dione 17-butyrate 21-disodium phosphate |
| 337 | 322 | 9α-Fluoro-11β,17α,21-trihydroxy-16α-methyl-5α-pregnane-3,20-dione 17-valerate 21-disodium phosphate |
| 338 | 323 | 9α-Fluoro-11β,17α,21-trihydroxy-16α-methyl-5α-pregnane-3,20-dione 17-benzoate 21-disodium phosphate |
| 339 | 324 | 9α-Fluoro-11β,17α,21-trihydroxy-5α-pregnane-3,20-dione 17-acetate 21-disodium phosphate |
| 340 | 325 | 9α-Fluoro-11β,17α,21-trihydroxy-5α-pregnane-3,20-dione 17-propionate 21-disodium phosphate |
| 341 | 326 | 9α-Fluoro-11β,17α,21-trihydroxy-5α-pregnane-3,20-dione 17-butyrate 21-disodium phosphate |
| 342 | 327 | 9α-Fluoro-11β,17α,21-trihydroxy-5α-pregnane-3,20-dione 17-valerate 21-disodium phosphate |
| 343 | 328 | 9α-Fluoro-11β,17α,21-trihydroxy-5α-pregnane-3, |

-continued

| Example | Column DDD | Column EEE |
|---|---|---|
| | | 20-dione-17-benzoate 21-disodium phosphate |

EXAMPLE 344

9α-Fluoro-11β,17α,21-trihydroxy-16β-methyl-5α-pregnane-3,20-dione 17-propionate 21-hemisuccinate (IV)

A mixture of 9α-fluoro-11β,17α,21-trihydroxy-16β-methyl-5α-pregnane-3,20-dione 17-propionate (Example 299, 5.4 g.) and succinic anhydride (5.6 g.) in pyridine (46 ml.) is stirred overnight at 20°–25°. The reaction mixture is then poured slowly into a stirred mixture of ice water (1 l.) containing hydrochloric acid (46 ml.). The precipitate is collected, washed thoroughly with water and dried to give the title compound.

EXAMPLES 345–358

Following the general procedure of Example 344, and making non-critical variations but starting with the 21-hydroxy steroids of Examples 299–313 (Column FFF), the 21-hemisuccinate esters of Column GGG are obtained.

| Example | Column FFF | Column GGG |
|---|---|---|
| 345 | 300 | 9α-Fluoro-11β,17α,21-trihydroxy-16β-methyl-5α-pregnane-3,20-dione 17-acetate 21-hemisuccinate |
| 346 | 301 | 9α-Fluoro-11β,17α,21-trihydroxy-16β-methyl-5α-pregnane-3,20-dione 17-butyrate 21-hemisuccinate |
| 347 | 302 | 9α-Fluoro-11β,17α,21-trihydroxy-16β-methyl-5α-pregnane-3,20-dione 17-valerate 21-hemisuccinate |
| 348 | 303 | 9α-Fluoro-11β,17α,21-trihydroxy-16β-methyl-5α-pregnane-3,20-dione 17-benzoate 21-hemisuccinate |
| 349 | 304 | 9α-Fluoro-11β,17α,21-trihydroxy-16α-methyl-5α-pregnane-3,20-dione 17-acetate 21-hemisuccinate |
| 350 | 305 | 9α-Fluoro-11β,17α,21-trihydroxy-16α-methyl-5α-pregnane-3,20-dione 17-propionate 21-hemisuccinate |
| 351 | 306 | 9α-Fluoro-11β,17α,21-trihydroxy-16α-methyl-5α-pregnane-3,20-dione 17-butyrate 21-hemisuccinate |
| 352 | 307 | 9α-Fluoro-11β,17α,21-trihydroxy-16α-methyl-5α-pregnane-3,20-dione 17-valerate 21-hemisuccinate |
| 353 | 308 | 9α-Fluoro-11β,17α,21-trihydroxy-16α-methyl-5α-pregnane-3,20-dione 17-benzoate 17-benzoate 21-hemisuccinate |
| 354 | 309 | 9α-Fluoro-11β,17α,21-trihydroxy-5α-pregnane-3,20-dione 17-acetate 21-hemisuccinate |
| 355 | 310 | 9α-Fluoro-11β,17α,21-trihydroxy-5α-pregnane-3,20-dione 17-propionate 21-hemisuccinate |
| 356 | 311 | 9α-Fluoro-11β,17α,21-trihydroxy-5α-pregnane-3,20-dione 17-butyrate 21-hemisuccinate |
| 357 | 312 | 9α-Fluoro-11β,17α,21-trihydroxy-5α-pregnane-3,20-dione 17-valerate 21-hemisuccinate |
| 358 | 313 | 9α-Fluoro-11β,17α,21-trihydroxy-5α-pregnane-3,20-dione 17-benzoate 21-hemisuccinate |

EXAMPLE 359

9α-Fluoro-11β,17α,21-trihydroxy-16β-methyl-5α-pregnane-3,20-dione 17-propionate 21-sodium hemisuccinate (IV)

A solution of 9α-fluoro-11β,17α,21-trihydroxy-16β-methyl-5α-pregnane-3,20-dione 17-propionate 21-hemisuccinate (Example 344, 1.63 g.) in acetone (10 ml.) is diluted with water (10 ml.) and a solution of sodium bicarbonate (0.248 g., 1.0 equivalent) in water (13.5 ml.) is added. The mixture is concentrated under reduced pressure and freeze-dried to give the title compound.

EXAMPLES 360-373

Following the general procedure of Example 359 and making non-critical variations but starting with the 21-hemisuccinate esters of Examples 345-358 (Column HHH), the 21-sodium hemisuccinate ester salts of Column III are obtained.

| Example | Column HHH | Column III |
|---|---|---|
| 360 | 345 | 9α-Fluoro-11β,17α,21-trihydroxy-16β-methyl-5α-pregnane-3,20-dione 17-acetate 21-sodium hemisuccinate |
| 361 | 346 | 9α-Fluoro-11β,17α,21-trihydroxy-16β-methyl-5α-pregnane-3,20-dione 17-butyrate 21-sodium hemisuccinate |
| 362 | 347 | 9α-Fluoro-11β,17α,21-trihydroxy-16β-methyl-5α-pregnane-3,20-dione 17-valerate 21-sodium hemisuccinate |
| 363 | 348 | 9α-Fluoro-11β,17α,21-trihydroxy-16β-methyl-5α-pregnane-3,20-dione 17-benzoate 21-sodium hemisuccinate |
| 364 | 349 | 9α-Fluoro-11β,17α,21-trihydroxy-16α-methyl-5α-pregnane-3,20-dione 17-acetate 21-sodium hemisuccinate |
| 365 | 350 | 9α-Fluoro-11β,17α,21-trihydroxy-16α-methyl-5α-pregnane-3,20-dione 17-propionate 21-sodium hemisuccinate |
| 366 | 351 | 9α-Fluoro-11β,17α,21-trihydroxy-16α-methyl-5α-pregnane-3,20-dione 17-butyrate 21-sodium hemisuccinate |
| 367 | 352 | 9α-Fluoro-11β,17α,21-trihydroxy-16α-methyl-5α-pregnane-3,20-dione 17-valerate 21-sodium hemisuccinate |
| 368 | 353 | 9α-Fluoro-11β,17α,21-trihydroxy-16α-methyl-5α-pregnane-3,20-dione 17-benzoate 21-sodium hemisuccinate |
| 369 | 354 | 9α-Fluoro-11β,17α,21-trihydroxy-5α-pregnane-3,20-dione 17-acetate 21-hemisuccinate |
| 370 | 355 | 9α-Fluoro-11β,17α,21-trihydroxy-5α-pregnane-3,20-dione 17-propionate 21-sodium hemisuccinate |
| 371 | 356 | 9α-Fluoro-11β,17α,21-trihydroxy-5α-pregnane-3,20-dione 17-butyrate 21-sodium hemisuccinate |
| 372 | 357 | 9α-Fluoro-11β,17α,21-trihydroxy-5α-pregnane-3,20-dione 17-valerate 21-sodium hemisuccinate |
| 373 | 358 | 9α-Fluoro-11β,17α,21-trihydroxy-5α-pregnane-3,20-dione 17-benzoate 21-sodium hemisuccinate |

EXAMPLES 374-382

Following the general procedure of Example 251, Step 2, and making non-critical variations but starting with the 17-propionate 21-acetate, 17,21-dipropionate, or 17-butyrate 21-acetate diesters of 17α,21-dihydroxy-16β-methyl-5α-pregn-9(11)-ene-3,20-dione, 17α,21-dihydroxy-16α-methyl-5α-pregn-9(11)ene-3,20-dione and 17α,21-dihydroxy-5α-pregn-9(11)-ene-3,20-dione (Examples 281-289), the corresponding 9,11-dichloro diesters, namely the 17-propionate 21-acetate, 17,21-dipropionate or 17-butyrate 21-acetate diesters of 9α,11β-dichloro-17α,21-dihydroxy-16β-methyl-5α-pregnane-3,20-dione, 9α,11β-dichloro-17α,21-dihydroxy-16α-methyl-5α-pregnane-3,20-dione and 9α,11β-dichloro-17α,21-dihydroxy-5α-pregnane-3,20-dione are obtained.

EXAMPLE 383

11β,17α,21-Trihydroxy-16β-methyl-5α-pregnane-3,20-dione 17,21-dipropionate (IV)

A solution of 9α-bromo-11β,17α,21-trihydroxy-16β-methyl-5α-pregnane-3,20-dione 17,21-dipropionate (Example 291, Step 1, 15.6 g.) in DMF (90 ml.) containing mercaptoacetic acid (12 ml.) is stirred at 20°-25° during the addition of aqueous chromous sulfate (35 ml.). The chromous sulfate is prepared from chromic sulfate hydrate (26.9 g.) and zinc (70 g., 30 mesh), stirred in water (66 ml.) for 16 hours under nitrogen. The steroid reaction mixture is stirred for several hours and then is diluted with water (400 ml.) and filtered. The crude product is dried and chromatographed on silica gel (670 g.), eluting with an acetone-methylene chloride mixture. The appropriate fractions are pooled and concentrated under reduced pressure to give the title compound.

EXAMPLES 384 AND 385

Following the general procedure of Example 383 and making non-critical variations but starting with the 17-propionate 21-acetate or 17-butyrate 21-acetate diesters of 9α-bromo-11β,17α,21-trihydroxy-16β-methyl-5α-pregnane-3,20-dione (Examples 290 and 292, Step 2), the corresponding 9-unsubstituted diesters, namely the 17-propionate 21-acetate or 17-butyrate 21-acetate diesters of 11β,17α,21-trihydroxy-16β-methyl-5α-pregnane-3,20-dione are obtained.

EXAMPLES 386-391

Following the general procedure of Example 383 and making non-critical variations but starting with the 17-propionate 21-acetate, 17,21-dipropionate or 17-butyrate 21-acetate diesters of 9α-bromo-11β,17α,21-trihydroxy-16α-methyl-5α-pregnane-3,20-dione and 9α-bromo-11β,17α,21-trihydroxy-5α-pregnane-3,20-dione (Examples 293-298, Step 1) the corresponding 9-unsubstituted diesters, namely the 17-propionate 21-acetate, 17,21-dipropionate or 17-butyrate 21-acetate diesters of 11β,17α,21-trihydroxy-16α-methyl-5α-pregnane-3,20-dione and 11β,17α,21-trihydroxy-5α-pregnane-3,20-dione are obtained.

EXAMPLES 392-406

Following the general procedure of Example 206, Step 3 and making non-critical variations but starting with the 21-mesylate of Examples 266-280 (Column JJJ) the 21-chloro steroids of Column KKK are obtained.

| Example | Column JJJ | Column KKK |
|---|---|---|
| 392 | 266 | 21-Chloro-11β,17α-dihydroxy-16β-methyl-5α-pregnane-3,20-dione 17-propionate |
| 393 | 267 | 21-Chloro-11β,17α-dihydroxy-16β-methyl-5α-pregnane-3,20-dione 17-acetate |
| 394 | 268 | 21-Chloro-11β,17α-dihydroxy-16β- |

-continued

| Example | Column JJJ | Column KKK |
|---|---|---|
| | | methyl-5α-pregnane-3,20-dione 17-butyrate |
| 395 | 269 | 21-Chloro-11β,17α-dihydroxy-16β-methyl-5α-pregnane-3,20-dione 17-valerate |
| 396 | 270 | 21-Chloro-11β,17α-dihydroxy-16β-methyl-5α-pregnane-3,20-dione 17-benzoate |
| 397 | 271 | 21-Chloro-11β,17α-dihydroxy-16α-methyl-5α-pregnane-3,20-dione 17-acetate |
| 398 | 272 | 21-Chloro-11β,17α-dihydroxy-16α-methyl-5α-pregnane-3,20-dione 17-propionate |
| 399 | 273 | 21-Chloro-11β,17α-dihydroxy-16α-methyl-5α-pregnane-3,20-dione 17-butyrate |
| 400 | 274 | 21-Chloro-11β,17α-dihydroxy-16α-methyl-5α-pregnane-3,20-dione 17-valerate |
| 401 | 275 | 21-Chloro-11β,17α-dihydroxy-16α-methyl-5α-pregnane-3,20-dione 17-benzoate |
| 402 | 276 | 21-Chloro-11β,17α-dihydroxy-5α-pregnane-3,20-dione 17-acetate |
| 403 | 277 | 21-Chloro-11β,17α-dihydroxy-5α-pregnane-3,20-dione 17-propionate |
| 404 | 278 | 21-Chloro-11β,17α-dihydroxy-5α-pregnane-3,20-dione 17-butyrate |
| 405 | 279 | 21-Chloro-11β,17α-dihydroxy-5α-pregnane-3,20-dione 17-valerate |
| 406 | 280 | 21-Chloro-11β,17α-dihydroxy-5α-pregnane-3,20-dione 17-benzoate |

CHART B

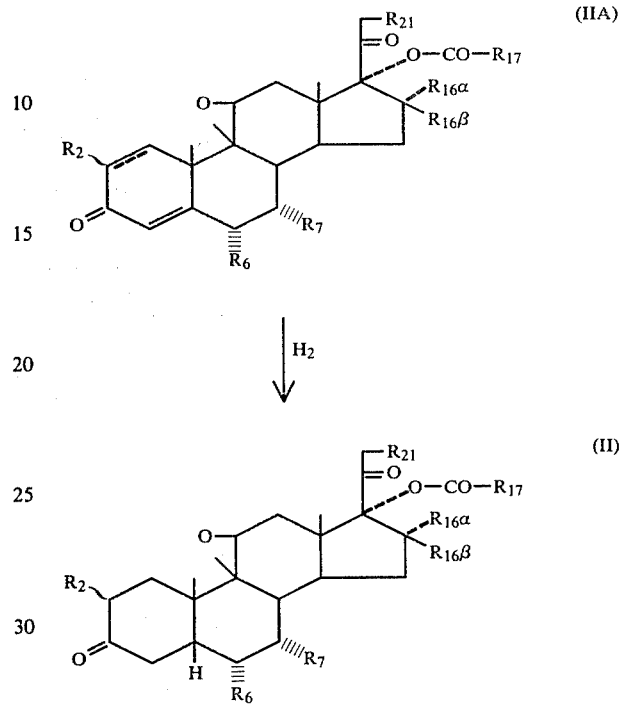

CHART A

CHART C

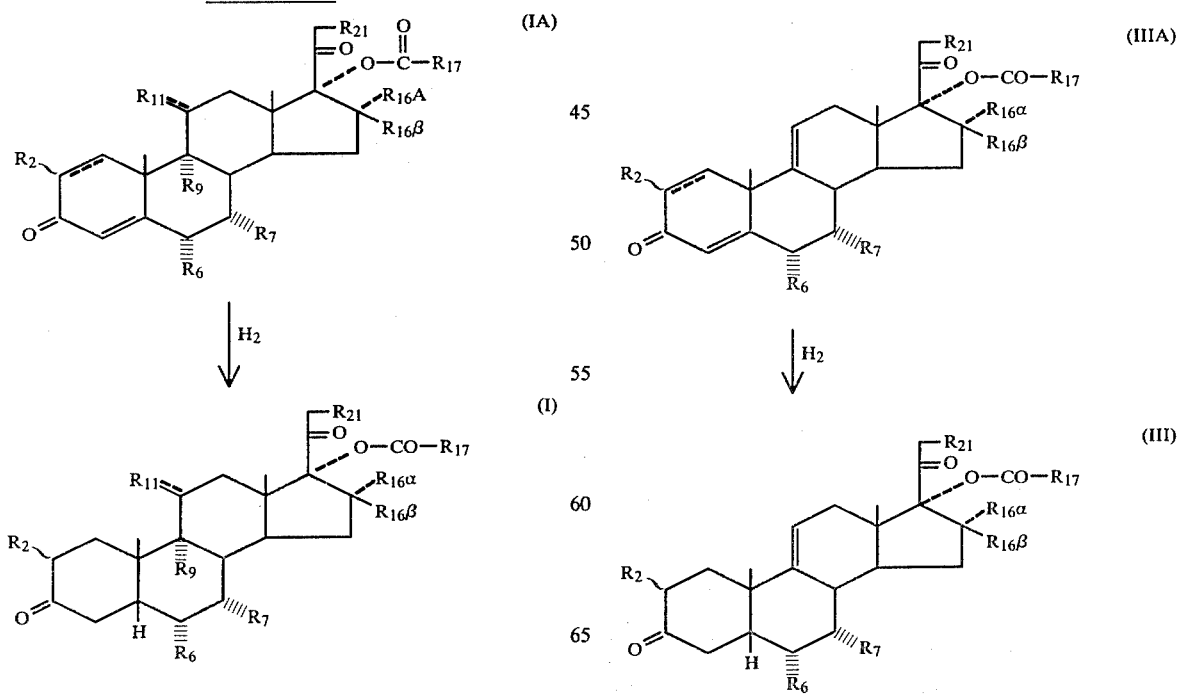

CHART D-1

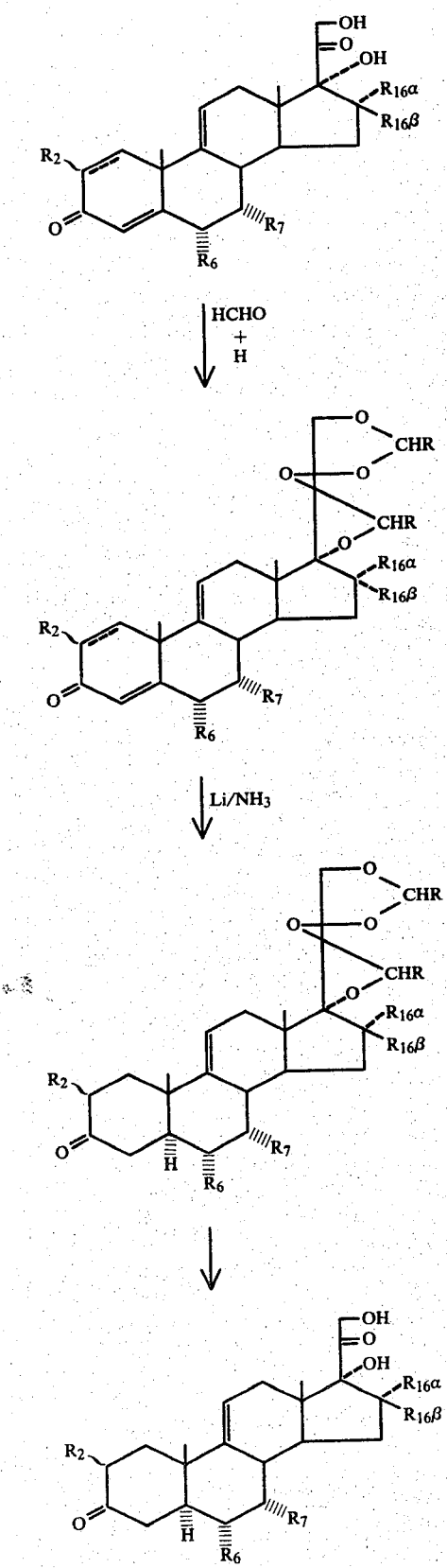

CHART D-2

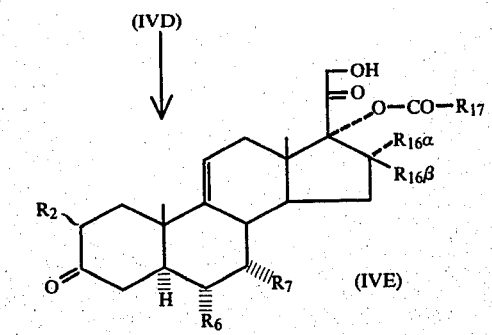

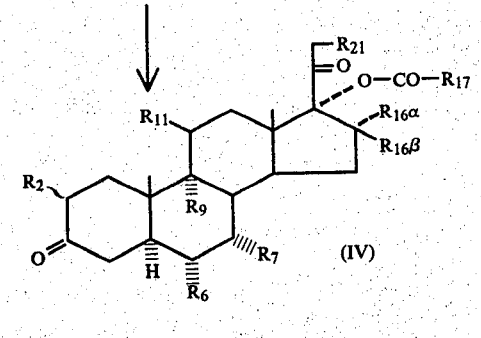

We claim:
1. A 5β-Δ$^{9(11)}$-steroid of the formula:

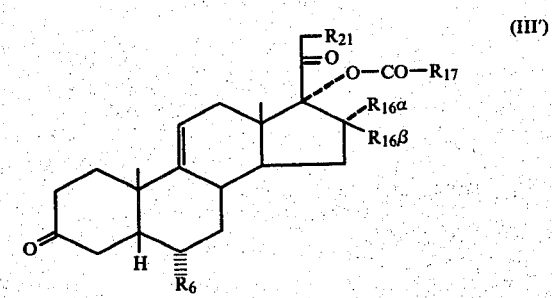

where
R$_6$ is hydrogen, fluorine or chlorine atom or methyl group;
R$_{16\alpha}$ is a hydrogen, fluorine or chlorine atom or methyl group;
R$_{16\beta}$ is a hydrogen atom or methyl group with the proviso that one of R$_{16\alpha}$ or R$_{16\beta}$ is a hydrogen atom;
R$_{17}$ is alkyl of 1 through 6 carbon atoms, phenyl, p-methylphenyl, p-carboxyphenyl or p-carboalkoxyphenyl;
R$_{21}$ is a hydrogen, fluorine, chlorine or bromine atom or a —OR$_{21a}$ or —OSO$_2$CH$_3$ group;
R$_{21a}$ is a hydrogen atom, —COR$_{21b}$ or —PO(OH)$_2$ and pharmaceutically acceptable salts thereof;
R$_{21b}$ is alkyl of 1 thru 6 carbon atoms, phenyl, p-methylphenyl, or p-carboxyphenyl, p-carboalkoxyphenyl, —CH$_2$CH$_2$COOH and pharmaceutically acceptable salts thereof; and
~ indicates the attached group can be in either the α or β configuration.
2. A 5α-Δ$^{9(11)}$-21-hydroxy-steroid of the formula

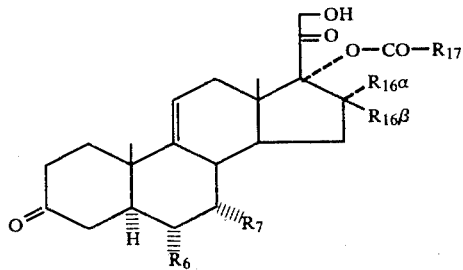 (IVE')

where $R_6$, $R_{16\alpha}$, $R_{16\beta}$, $R_{17}$ and $\sim$ are defined in claim 1.

3. A compound according to claim 2 where $R_2$ and $R_7$ are hydrogen atoms and $R_{16\beta}$ is methyl.

4. A compound according to claim 2 where $R_2$ and $R_7$ are a hydrogen atom and $R_{16\alpha}$ is methyl.

5. A compound according to claim 2 where $R_2$, $R_7$, $R_{16\alpha}$ and $R_{16\beta}$ are hydrogen atoms.

6. 17α,21-Dihydroxy-16β-methyl-5α-pregn-9(11)-ene-3,20-dione 17-propionate 21-mesylate.

7. A process for preparing a 5β-Δ$^{9(11)}$-steroid of the formula:

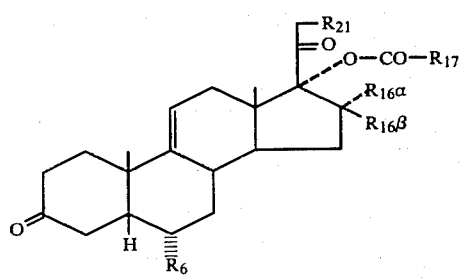 (III')

which comprises
(1) hydrogenating a compound of the formula:

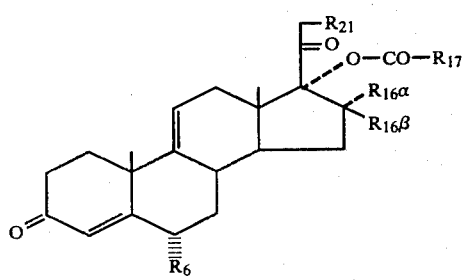 (IIIA')

in the presence of a hydrogenating catalyst selected from the group consisting of palladium on carbon, platinum on carbon, platinum dioxide, pallodium on barium carbonate, polladium on calcium carbonate, rhodium on alumina, rhodium on carbon, polladium on barium sulfate, polladium on zinc oxide, tris(triphenylphosphine)rhodium (I) chloride, (2) separating the 5β-isomer from the 5α-isomer where $R_6$, $R_{16\alpha}$, $R_{16\beta}$, $R_{17}$, $R_{21}$, and $\sim$, are defined in claim 1 and where . . . is a single or double bond.

8. A process according to claim 7 where $R_6$ is a hydrogen or fluorine atom or methyl group.

9. A process according to claim 8 where $R_6$ is a hydrogen atom.

10. A process according to claim 7 where $R_{16\alpha}$ is a hydrogen atom or methyl group.

11. A process according to claim 7 where $R_{16\beta}$ is a hydrogen atom or methyl group.

12. A process according to claim 7 where $R_{17}$ is alkyl of 1 thru 5 carbon atoms, phenyl, or paramethylphenyl.

13. A process according to claim 12 where $R_{17}$ is alkyl of 1 thru 4 carbon atoms or phenyl.

14. A process according to claim 7 where $R_{21}$ is a hydrogen, fluorine, or chlorine atom or a —OR$_{21a}$ group where $R_{21a}$ is defined in claim 1.

15. A process according to claim 14 where $R_{21}$ is a hydrogen or chlorine atom or —OR$_{21a}$ group where $R_{21a}$ is —COR$_{21b}$ where $R_{21b}$ is defined in claim 1.

16. A process for preparing a 5α-17α,21-dihydroxy steroid of the formula

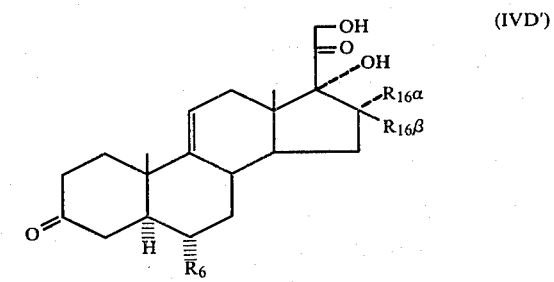 (IVD')

which comprises:
(1) blocking the side chain of a Δ$^4$-17α,21-dihydroxy-20-keto steroid of the formula

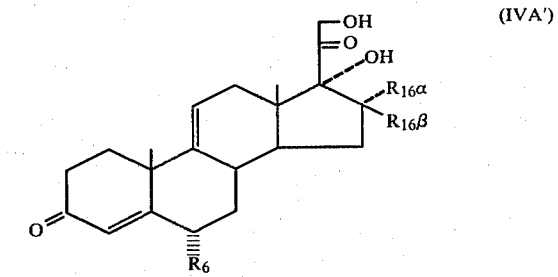 (IVA')

by reaction with an aldehyde of the formula R—CHO to give a Δ$^4$-17,21-blocked steroid of the formula

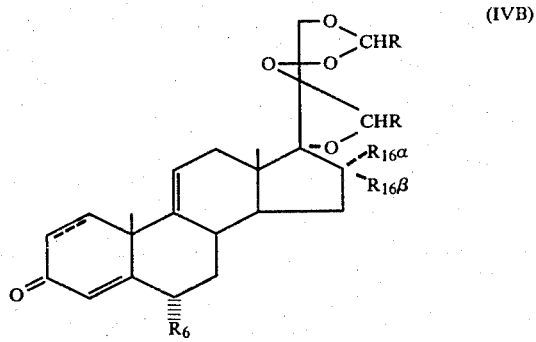 (IVB)

(2) reducing the Δ$^4$-double bond by reaction with a metal-amine to give the 5α-17α,21-blocked steroid of the formula

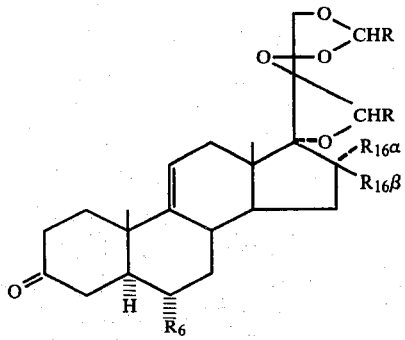

and (3) removing the 17,21-blocking group where $R_6$, $R_{11}$, $R_{16\alpha}$ and $R_{16\beta}$ are defined in claim 1 and where R is a hydrogen atom or alkyl group of 1 through 4 carbon atoms.

17. A process according to claim 16 wherein $R_{16\alpha}$ is a methyl group.

18. A process according to claim 16 where $R_{16\beta}$ is a methyl group.

19. A process according to claim 16 where $R_{16\alpha}$ and $R_{16\beta}$ are both hydrogen atoms.

20. A process according to claim 16 where the 17,21-blocking group is removed with dilute acid.

21. A process according to claim 16 where the lithium-ammonia reduction is performed at less than $-35°$.

22. A process according to claim 16 where the metal of the metal-amine is lithium or sodium.

23. A process according to claim 22 where the metal is lithium.

24. A process according to claim 16 where the amine of the metal-amine is selected from the group consisting of ammonia, methylamine, ethylamine or ethylenediamine.

25. A process according to claim 24 where the amine is ammonia.

26. A process according to claim 25 where the metal-amine is selected from the group consisting of lithium-ammonia or sodium-ammonia.

27. A process according to claim 16 where R is a hydrogen atom.

28. A compound according to claim 1 which is $17\alpha,21$-dihydroxy-$16\beta$-methyl-$5\beta$-pregn-9(11)-ene-3,20-dione 17,21-dipropionate.

29. A compound according to claim 1 which is $17\alpha,21$-dihydroxy-$16\alpha$-methyl-$5\beta$-pregn-9(11)-ene-3,20-dione 17,21-dipropionate.

30. A compound according to claim 1 which is $17\alpha,21$-dihydroxy-$5\beta$-pregn-9(11)-ene-3,20-dione 17,21-dipropionate.

31. A compound according to claim 1 which is $17\alpha,21$-dihydroxy-$16\beta$-methyl-$5\beta$-pregn-9(11)-ene-3,20-dione 17-propionate 21-mesylate.

32. A compound according to claim 1 which is $17\alpha,21$-dihydroxy-$16\alpha$-methyl-$5\beta$-pregna-9(11)-ene-3,20-dione 17-propionate 21-mesylate.

33. A compound according to claim 1 which is $17\alpha,21$-dihydroxy-$5\beta$-pregna-9(11)-ene-3,20-dione 17-propionate 21-mesylate.

34. A compound according to claim 1 which is 21-chloro-$17\alpha$-hydroxy-$16\beta$-methyl-$5\beta$-pregn-9(11)-ene-3,20-dione 17-propionate.

35. A compound according to claim 1 which is 21-chloro-$17\alpha$-hydroxy-$16\alpha$-methyl-$5\beta$-pregn-9(11)-ene-3,20-dione 17-propionate.

36. A compound according to claim 1 which is 21-chloro-$17\alpha$-hydroxy-$5\beta$-pregn-9(11)-ene-3,20-dione 17-propionate.

37. A compound according to claim 3 which is $17\alpha,21$-dihydroxy-$16\beta$-methyl-$5\alpha$-pregn-9(11)-ene-3,20-dione 17-propionate.

38. A compound according to claim 3 which is $17\alpha,21$-dihydroxy-$16\beta$-methyl-$5\alpha$-pregn-9(11)-ene-3,20-dione 17-acetate.

39. A compound according to claim 3 which is $17\alpha,21$-dihydroxy-$16\beta$-methyl-$5\alpha$-pregn-9(11)-ene-3,20-dione 17-butyrate.

40. A compound according to claim 3 which is $17\alpha,21$-dihydroxy-$16\beta$-methyl-$5\alpha$-pregn-9(11)-ene-3,20-dione 17-valerate.

41. A compound according to claim 3 which is $17\alpha,21$-dihydroxy-$16\beta$-methyl-$5\alpha$-pregn-9(11)-ene-3,20-dione 17-benzoate.

42. A compound according to claim 4 which is $17\alpha,21$-dihydroxy-$16\alpha$-methyl-$5\alpha$-pregn-9(11)-ene-3,20-dione 17-acetate.

43. A compound according to claim 4 which is $17\alpha,21$-dihydroxy-$16\alpha$-methyl-$5\alpha$-pregn-9(11)-ene-3,20-dione 17-propionate.

44. A compound according to claim 4 which is $17\alpha,21$-dihydroxy-$16\alpha$-methyl-$5\alpha$-pregn-9(11)-ene-3,20-dione 17-butyrate.

45. A compound according to claim 4 which is $17\alpha,21$-dihydroxy-$16\alpha$-methyl-$5\alpha$-pregn-9(11)-ene-3,20-dione 17-valerate.

46. A compound according to claim 4 which is $17\alpha,21$-dihydroxy-$16\alpha$-methyl-$5\alpha$-pregn-9(11)-ene-3,20-dione 17-benzoate.

47. A compound according to claim 5 which is $17\alpha,21$-dihydroxy-$5\alpha$-pregn-9(11)-ene-3,20-dione 17-acetate.

48. A compound according to claim 5 which is $17\alpha,21$-dihydroxy-$5\alpha$-pregn-9(11)-ene-3,20-dione 17-propionate.

49. A compound according to claim 5 which is $17\alpha,21$-dihydroxy-$5\alpha$-pregn-9(11)-ene-3,20-dione 17-butyrate.

50. A compound according to claim 5 which is $17\alpha,21$-dihydroxy-$5\alpha$-pregn-9(11)-ene-3,20-dione 17-valerate.

51. A compound according to claim 5 which is $17\alpha,21$-dihydroxy-$5\alpha$-pregn-9(11)-ene-3,20-dione 17-benzoate.

52. A process according to claim 7 where the $5\beta$-$\Delta^{9(11)}$-steroid (III) is $17\alpha,21$-dihydroxy-$16\beta$-methyl-$5\beta$-pregn-9(11)-ene-3,20-dione 17,21-dipropionate.

53. A process according to claim 7 where the $5\beta$-$\Delta^{9(11)}$-steroid (III) is $17\alpha,21$-dihydroxy-$16\alpha$-methyl-$5\beta$-pregn-9(11)-ene-3,20-dione 17,21-dipropionate.

54. A process according to claim 7 where the $5\beta$-$\Delta^{9(11)}$-steroid (III) is $17\alpha,21$-dihydroxy-$5\beta$-pregn-9(11)-ene-3,20-dione 17,21-dipropionate.

55. A process according to claim 7 where the $5\beta$-$\Delta^{9(11)}$-steroid (III) is $17\alpha,21$-dihydroxy-$16\beta$-methyl-$5\beta$-pregn-9(11)-ene-3,20-dione 17-propionate 21-mesylate.

56. A process according to claim 7 where the $5\beta$-$\Delta^{9(11)}$-steroid (III) is $17\alpha,21$-dihydroxy-$16\alpha$-methyl-$5\beta$-pregna-9(11)-ene-3,20-dione 17-propionate 21-mesylate.

57. A process according to claim 7 where the 5β-Δ$^{9(11)}$-steroid (III) is 17α,21-dihydroxy-5β-pregna-9(11)-ene-3,20-dione 17-propionate 21-mesylate.

58. A process according to claim 7 where the 5β-Δ$^{9(11)}$-steroid (III) is 21-chloro-17α-hydroxy-16β-methyl-5β-pregn-9(11)-ene-3,20-dione 17-propionate.

59. A process according to claim 7 where the 5β-Δ9(11)-steroid (III) is 21-chloro-17α-hydroxy-16α-methyl-5β-pregn-9-(11)-ene-3,20-dione 17-propionate.

60. A process according to claim 7 where the 5β-Δ9(11)-steroid (III) is 21-chloro-17α-hydroxy-5β-pregn-9(11)-ene-3,20-dione 17-propionate.

* * * * *

UNITED STATES PATENT OFFICE
CERTIFICATE OF CORRECTION

Patent No. 4,427,591  Dated January 24, 1984

Inventor(s) Donald E. Ayer et al.

It is certified that error appears in the above-identified patent and that said Letters Patent are hereby corrected as shown below:

Column 2, line 41, "a Δ-17,21-blocked steroid" should read
--a $\Delta^4$-17,21-blocked steroid--
Column 2, line 49, "readily by hydrogenating" should read
--readily prepared by hydrogenating--
Column 6, line 53, "dichloroxime" should read --dichloroxine--
Column 10, line 14, "the 17,23-" should read --the 17,21---
Column 21, line 9, "43°" should read --+43°--
Column 21, line 9, "CMF" should read --CMR--
Column 21, line 37, "-11α17α" should read ---11β,17α--
Column 21, line 49-50, "1105,990" should read --1105,1025,990--
Column 22, line 45, "CMF" should read --CMR--
Column 25, line 18,  Column II    Column JJ
                     "17-benzoate
                     benzoate"                should read
                     Column II    Column JJ
                  -- 17-benzoate  benzoate--
Column 26, line 28, "triethylene" should read --triethylamine--
Column 32, line 28, "11β,11α" should read --11β,17α--
Column 33, line 23, "Example 160, 1.53 g" should read --Example 160, 1.63 g--

UNITED STATES PATENT OFFICE
CERTIFICATE OF CORRECTION

Patent No. 4,427,591　　　　　　　　　Dated January 24, 1984

Inventor(s) Donald E. Ayer et al.

It is certified that error appears in the above-identified patent and that said Letters Patent are hereby corrected as shown below:

Column 39, line 57, "dihydroxy-6α" should read --dihydroxy-16α--

Signed and Sealed this

Eighteenth Day of June 1985

[SEAL]

Attest:

DONALD J. QUIGG

Attesting Officer　　　Acting Commissioner of Patents and Trademarks